US012797131B2

(12) United States Patent
Chauhan et al.

(10) Patent No.: US 12,797,131 B2
(45) Date of Patent: Nov. 17, 2026

(54) SYSTEM AND METHOD FOR AUTOMATED FOCAL SOURCE DETECTION

(71) Applicant: UNIVERSITY HEALTH NETWORK, Toronto (CA)

(72) Inventors: Vijay Singh Chauhan, Toronto (CA); Bo Wang, Maple (CA); Shun Liao, Oakville (CA)

(73) Assignee: UNIVERSITY HEALTH NETWORK, Toronto (CA)

( * ) Notice: Subject to any disclaimer, the term of this patent is extended or adjusted under 35 U.S.C. 154(b) by 272 days.

(21) Appl. No.: 18/422,510

(22) Filed: Jan. 25, 2024

(65) Prior Publication Data

US 2024/0156536 A1 May 16, 2024

Related U.S. Application Data

(63) Continuation of application No. PCT/CA2022/051145, filed on Jul. 25, 2022.

(Continued)

(51) Int. Cl.
*A61B 34/10* (2016.01)
*A61B 5/00* (2006.01)
*A61B 5/346* (2021.01)

(52) U.S. Cl.
CPC .............. *A61B 34/10* (2016.02); *A61B 5/346* (2021.01); *A61B 5/7267* (2013.01)

(58) Field of Classification Search
CPC ........ G06N 3/0464; G06N 3/048; G06N 3/09; G06N 3/0985; A61B 34/10; A61B 5/283;

(Continued)

(56) References Cited

U.S. PATENT DOCUMENTS

| | | | | |
|---|---|---|---|---|
| 10,111,598 B2 * | 10/2018 | Chauhan | ............ | A61B 18/1492 |
| 2013/0150740 A1 * | 6/2013 | Narayan | .............. | A61B 5/7257 600/508 |

(Continued)

FOREIGN PATENT DOCUMENTS

WO 2020226534 A1 11/2020

OTHER PUBLICATIONS

Hannun, A. Y., Rajpurkar, P., Haghpanahi, M., Tison, G. H., Bourn, C., Turakhia, M. P., & Ng, A. Y. (2019). Cardiologist-level arrhythmia detection and classification in ambulatory electrocardiograms using a deep neural network. Nature Medicine, 25(1), 65-69 (Year: 2019).*

(Continued)

*Primary Examiner* — Scott Luan

(57) ABSTRACT

Various embodiments are described herein for a system, method, and device for automated detection of focal source locations of electrophysiological activity in an organ. The system, method and device may also be used to guide catheter ablation of the organ. An electrogram signal can be obtained from a location in the organ, and it can be determined if the electrogram is periodic. If so, the corresponding unipolar electrogram can be input to a deep learning neural network classification model trained to generate a unipolar electrogram classification result in response to receiving the unipolar electrogram as an input. The location can be identified as a focal source location or a non-focal source location based on the unipolar electrogram classification result.

20 Claims, 10 Drawing Sheets

Related U.S. Application Data

(60) Provisional application No. 63/225,996, filed on Jul. 27, 2021.

(58) Field of Classification Search
CPC ......... A61B 5/346; A61B 5/347; A61B 5/349; A61B 5/361; A61B 5/366; A61B 5/7264; A61B 5/7267
See application file for complete search history.

(56) References Cited

U.S. PATENT DOCUMENTS

| | | | | |
|---|---|---|---|---|
| 2017/0079539 A1* | 3/2017 | Chauhan | .............. | A61B 5/7264 |
| 2022/0346856 A1* | 11/2022 | Fedorov | ............... | A61B 5/7267 |

OTHER PUBLICATIONS

Debakker et al., "The pathophysiologic basis of fractionated and complex electrograms and the impact of recording techniques on their detection and interpretation", Circ Arrhythm Electrophysiol, Apr. 2010, vol. 3(2), pp. 204-213.
Pedregosa et al., "Scikit-learn: Machine learning in Python", Journal of Machine Learning Research, 2011, vol. 12, pp. 2825-2830.
He et al., "Delving deep into rectifiers: Surpassing human-level performance on imagenet classification", Proceedings of the IEEE international conference on computer vision, 2015, pp. 1026-1034.
Gizurarson et al., "Hierarchical Schema for Identifying Focal Electrical Sources During Human Atrial Fibrillation: Implications for Catheter-Based Atrial Substrate Ablation", JACC Clinical Electrophysiology, 2016, vol. 2(6), pp. 656-666.
He et al., "Identity mappings in deep residual networks", European conference on computer vision, Oct. 2016, pp. 630-645.
Heijman et al., "The value of basic research insights into atrial fibrillation mechanisms as a guide to therapeutic innovation: a critical analysis", Cardiovascular Research, 2016 , vol. 109(4), pp. 467-479.
Selvaraju et al., "Grad-CAM: Visual Explanations from Deep Networks via Gradient-based Localization", Proceedings of the IEEE international conference on computer vision, 2017, pp. 618-626.
Brownlee, "How to Configure the No. of Layers and Nodes in a Neural Network", Deep Learning Performance, Aug. 6, 2019.
Hannun et al., "Cardiologist-level arrhythmia detection and classification in ambulatory electrocardiograms using a deep neural network", Nature Medicine, Jan. 2019, vol. 25, pp. 65-69.
Paszke et al., "An imperative style, high-performance deep learning library", 33rd Conference on Neural Information Processing Systems (NeurIPS 2019), pp. 8026-8037.
Shorten et al., "A survey on image data augmentation for deep learning", Journal of Big Data, 2019; 6(1), pp. 1-48.
Xu et al., "Towards End-to-End ECG Classification with Raw Signal Extraction and Deep Neural Networks", IEEE Journal of Biomedical and Health Informatics, Jul. 2019, vol. 23(4), pp. 1574-1584.
Liao et al., "Deep Learning Classification of Unipolar Electrograms in Human Atrial Fibrillation: Application in Focal Source Mapping", Fronters in Physiology, Jul. 2021, vol. 12 (article 704122), pp. 1-12.
International Search Report and Written Opinion mailed Oct. 6, 2022 in PCT/CA2022/05145.
Ganesan et al., "Long-term outcomes of catheter ablation of atrial fibrillation: a systematic review and meta-analysis", Journal of the American Heart Associated, Mar. 2013, vol. 2(2), pp. 1-14 (e004549).
Lee et al., "Reconsidering the multiple wavelet hypothesis of atrial fibrillation", Heart Rhythm, Nov. 2020, vol. 17 (11), pp. 1976-1983.
Lee et al., "High density mapping of atrial fibrillation during vagal nerve stimulation in the canine heart: restudying the Moe hypothesis", Journal of Cardiovascular Electrophysiology, Mar. 2013, vol. 24(3), pp. 328-335.
Roney et al., "Spatial Resolution Requirements for Accurate Identification of Drivers of Atrial Fibrillation", Circ Arrhythm Electrophysiol, May 2017, vol. 10(5), pp. 1-13 (e004899).
Kochhauser et al., "Spatial Relationships of Complex Fractionated Atrial Electrograms and Continuous Electrical Activity to Focal Electrical Sources: Implications for Substrate Ablation in Human Atrial Fibrillation", JACC Clinical Electrophysiology, 2017, vol. 3(11), pp. 1220-1228.
Chauhan et al., "Focal source and trigger mapping in atrial fibrillation: Randomized controlled trial evaluating a novel adjunctive ablation strategy", Heart Rhythm Society, May 2020, vol. 17(5PA), pp. 683-691.
Nayyar et al., "Focal and pseudo/rotational activations in human atrial fibrillation defined with automated periodicity mapping", J Cardiovasc Electrophysiol, 2021, vol. 32, pp. 212-223.
Papernot et al., "The limitations of deep learning in adversarial settings", IEEE European symposium on security and privacy, IEEE 2016, pp. 372-387.
Chang et al., "Usefulness of Machine Learning-Based Detection and Classification of Cardiac Arrhythmias With 12-Lead Electrocardiograms", Canadian Journal of Cardiology, 2021, vol. 37, pp. 94-104.
Feeny et al., "Artificial Intelligence and Machine Learning in Arrhythmias and Cardiac Electrophysiology", Circ Arrhythm Electrophysiol, Aug. 2020, vol. 13(8), pp. 873-890 (e007952).
Dalvi et al., "Identification and annotation of multiple periodic pulse trains using dominant frequency and graph search: Applications in atrial fibrillation rotor detection", Annu Int Conf IEEE Eng Med Biol Soc, Aug. 2016, pp. 3572-3575.
Wang et al., "The effectiveness of data augmentation in image classification using deep learning", Dec. 2017, arXiv: 1712 04621 2017;Dec. 13:[e-print].
Lecun et al., "Deep learning", Nature, 2015, vol. 521, pp. 436-444.
Kingma et al., "Adam: A method for stochastic optimization", arXiv: 1412 6980 2014; Dec:[e-print].
Saito et al., "The precision-recall plot is more informative than the ROC plot when evaluating binary classifiers on imbalanced datasets", PLoS One, 2015, vol. 10(3), pp. 1-21 (e0118432.).
Lee et al., "Characterization of Foci and Breakthrough Sites During Persistent and Long-Standing Persistent Atrial Fibrillation in Patients: Studies Using High-Density (510-512 Electrodes) Biatrial Epicardial Mapping", Journal of the American Heart Association, Mar. 2017, vol. 6(3), pp. 1-12.
Lee et al., "Simultaneous Biatrial High-Density (510-512 Electrodes) Epicardial Mapping of Persistent and Long-Standing Persistent Atrial Fibrillation in Patients: New Insights Into the Mechanism of Its Maintenance", Circulation, Dec. 2015, vol. 132(22), pp. 2108-2117.
Alhusseini et al., "Machine Learning to Classify Intracardiac Electrical Patterns During Atrial Fibrillation: Machine Learning of Atrial Fibrillation", Circ Arrhythm Electrophysiol, Aug. 2020, vol. 13(8), pp. 719-729 (e008160.).
Zolotarev et al., "Optical Mapping-Validated Machine Learning Improves Atrial Fibrillation Driver Detection by Multi-Electrode Mapping", Circ Arrhythm Electrophysiol, Oct. 2020, vol. 13(10), pp. 1199-1212 (e008249).
Bleijendaal et al. "Computer versus cardiologist: Is a machine learning algorithm able to outperform an expert in diagnosing a phospholamban p.Arg14del mutation on the electrocardiogram?", Heart Rhythm, Jan. 2021, vol. 18 (1), pp. 79-87.

* cited by examiner

SYSTEM AND METHOD FOR AUTOMATED FOCAL SOURCE DETECTION

CROSS-REFERENCE TO RELATED APPLICATION(S)

This application is a continuation of International Application No. PCT/CA2022/051145, filed on Jul. 25, 2022, which claims priority to U.S. Provisional Patent Application No. 63/225,996, filed on Jul. 27, 2021. The entire content of PCT/CA2022/051145 and U.S. 63/225,996 is incorporated herein by reference.

FIELD

The various embodiments described herein generally relate to a system and method for identifying focal source locations of electrophysiological activity in an organ.

INTRODUCTION

The following is not an admission that anything discussed below is part of the prior art or part of the common general knowledge of a person skilled in the art.

Abnormal electrical rhythms in the heart or brain can arise from repetitively firing electrical impulses, sometimes known as focal sources (FS) or triggers. These electrical impulses generate electrical propagating waves in the heart or brain which spread out and collide with one another to create chaotic electrical rhythms. Locating these focal sources and triggers is often essential to treat these abnormal electrical rhythms.

Atrial fibrillation (AF) is a common cardiac arrhythmia characterized by chaotic electric activity in the heart. Computational, animal and human studies have indicated that AF can, in some instances, be driven by discrete periodic focal sources with high frequency. However, finding these focal sources remains a challenge.

A common therapy for AF is catheter ablation where heat energy is delivered to the atrium in order to stop AF. However, standard AF catheter ablation does not work well despite extensive burning in the atrium because the ablation sites may not reliably target the focal sources or triggers that cause AF. Thus, a significant number of patients develop AF recurrence after ablation and need another ablation procedure. Given the prevalence of AF in society, its disabling health consequences, and the constraints on healthcare costs, the success rate of AF ablation must be improved.

SUMMARY OF VARIOUS EMBODIMENTS

The following introduction is provided to introduce the reader to the more detailed discussion to follow. The introduction is not intended to limit or define any claimed or as yet unclaimed invention. One or more inventions may reside in any combination or sub-combination of the elements or process steps disclosed in any part of this document including its claims and figures.

In accordance with a broad aspect, there is provided a method of identifying one or more focal source locations of electrophysiological activity for an organ, the method comprising: receiving a first electrical signal set obtained from a first location of the organ, wherein the first electrical signal set comprises a unipolar electrogram; determining that the first electrical signal set is periodic; upon determining that the first electrical signal set is periodic, generating a unipolar electrogram classification result by inputting the unipolar electrogram to a deep learning neural network classification model wherein the deep learning neural network classification model is trained to generate the unipolar electrogram classification result in response to receiving the unipolar electrogram as an input; and identifying the first location in the organ as a first focal source location of the one or more focal source locations based on the unipolar electrogram classification result.

In some examples, identifying the first location in the organ as a first focal source location may include comparing the unipolar electrogram classification result to a focal source identification threshold parameter; and identifying the first location in the organ as a first focal source location of the one or more focal source locations when the unipolar electrogram classification result meets or exceeds the focal source identification threshold parameter.

In some examples, the deep learning neural network classification model may be configured to generate the unipolar electrogram classification result as a probability value that the unipolar electrogram corresponds to a focal source location; and the focal source identification threshold parameter corresponds to a sensitivity of at least 85%.

In some examples, the focal source identification threshold parameter may correspond to a sensitivity in a range between about 85%-95%.

In some examples, the focal source identification threshold parameter may correspond to a sensitivity of about 90%.

In some examples, the first electrical signal set may include a bipolar electrogram and determining that the first electrical signal set is periodic may include analyzing the bipolar electrogram to identify periodicity in the bipolar electrogram.

In some examples, analyzing the bipolar electrogram to identify periodicity may include determining that a peak spectral power of the bipolar electrogram satisfies a threshold power level.

In some examples, determining that the peak spectral power of the bipolar electrogram satisfies the threshold power level may include determining a total spectral power of the bipolar electrogram; determining the peak spectral power; and determining that the peak spectral power is at least 10% of the total spectral power.

In some examples, the method may include pre-processing the bipolar electrogram prior to analyzing the bipolar electrogram to identify periodicity, where pre-processing the bipolar electrogram may include: filtering the bipolar electrogram using a bandpass filter; rectifying the filtered bipolar electrogram; and calculating a fast Fourier transform of the rectified bipolar electrogram.

In some examples, the method may include determining unipolar electrogram periodicity based on periodicity in the corresponding bipolar electrogram. For example, the presence of periodicity in the bipolar electrogram can be used to define periodicity in the corresponding unipolar electrogram (i.e. the unipolar electrogram corresponding to the bipolar electrogram).

In some examples, determining that the first electrical signal set is periodic may include identifying the unipolar electrogram as a periodic unipolar electrogram based on the presence of periodicity in the bipolar electrogram.

In some examples, the deep learning neural network classification model may be configured to generate the unipolar electrogram classification result using only the unipolar electrogram as an input from the first electrical signal set.

In some examples, the deep learning neural network classification model may use a residual convolutional neural network.

In some examples, the residual convolutional neural network may be defined using one-dimensional convolution filters.

In some examples, the deep learning neural network classification model may use an artificial neural network having 18 layers of neural nodes.

In some examples, the deep learning neural network classification model may be trained using raw unipolar electrogram data.

In some examples, the deep learning neural network classification model may be trained using augmented unipolar electrogram data.

In some examples, the augmented unipolar electrogram data may include multiple copies of the same raw unipolar electrogram data, where each copy has a different augmentation applied thereto.

In some examples, the method may include generating the augmented unipolar electrogram data by: normalizing the raw unipolar electrogram data; and at least one of baseline shifting the raw unipolar electrogram data using a constant noise signal; adding a Gaussian distribution of noise to the raw unipolar electrogram data; randomly cropping the raw unipolar electrogram data by replacing a segment of the raw unipolar electrogram data with zeros; or resampling the raw unipolar electrogram data.

In some examples, the method may include receiving a plurality of additional electrical signal sets, each of the additional electrical signal sets being obtained from different locations in the organ, and each of the additional electrical signal sets including an additional unipolar electrogram; determining that a given additional electrical signal set is periodic; upon determining that the given additional electrical signal set is periodic, generating an additional unipolar electrogram classification result by inputting the additional unipolar electrogram from that given additional electrical signal set to the deep learning neural network classification model; and identifying an additional location in the organ that corresponds to the given additional electrical signal set as an additional focal source location of the one or more focal source locations based on the additional unipolar electrogram classification result.

In some examples, the organ may be a heart.

In some examples, the electrophysiological activity may be atrial fibrillation or ventricular fibrillation.

In some examples, the deep learning neural network classification model may be trained to detect the presence or absence of predominantly sustained, periodic unipolar QS complexes in the unipolar electrogram and to generate the unipolar electrogram classification result based on the detected presence or absence of the predominantly sustained, periodic unipolar QS complexes.

In accordance with a broad aspect, there is provided a computer readable medium comprising a plurality of instructions that are executable on a microprocessor of a device for adapting the device to implement a method of identifying one or more focal source locations of electrophysiological activity for an organ, wherein the method is described herein.

In accordance with a broad aspect, there is provided an electronic device for identifying one or more focal source locations of electrophysiological activity for an organ, the electronic device comprising: an input operable to receive a first electrical signal set obtained from a first location of the organ, wherein the first electrical signal set comprises a unipolar electrogram; a processor coupled to the input, the processor configured to receive the first electrical signal set from the input and to determine that the first electrical signal set is periodic; upon determining that the first electrical signal set is periodic, generate a unipolar electrogram classification result by inputting the unipolar electrogram to a deep learning neural network classification model wherein the deep learning neural network classification model is trained to generate the unipolar electrogram classification result in response to receiving the unipolar electrogram as an input; and identify the first location in the organ as a first focal source location of the one or more focal source locations based on the unipolar electrogram classification result; and an output coupled to the processing unit to indicate any identified focal source locations for the organ.

In some examples, the processor may be further configured to perform the method as described herein.

In accordance with a broad aspect, there is provided a system for identifying one or more focal source locations of electrophysiological activity for an organ and guiding catheter ablation of the one or more focal source locations, wherein the system comprises a device as described herein and an ablation unit usable to perform catheter ablation.

In accordance with a broad aspect, there is provided a data processing system comprising: a non-transitory computer readable medium storing computer readable instructions and a data structure defining a deep learning neural network classification model configured to generate a unipolar electrogram classification result, wherein the data structure comprises a plurality of nodes, each node having a node input and a node output, and the plurality of nodes being arranged into a plurality of layers of nodes including at least one input layer and at least one output layer; and a computer processor operable to execute the computer readable instructions stored on the computer readable medium using the data structure to identify one or more focal source locations of electrophysiological activity for an organ; wherein the computer readable instructions are defined to configure the computer processor to: receive a first electrical signal set obtained from a first location of the organ, wherein the first electrical signal set comprises a unipolar electrogram; determine that the first electrical signal set is periodic; upon determining that the first electrical signal set is periodic, input the unipolar electrogram to the data structure; receive the unipolar electrogram classification result as an output from the data structure; and identify the first location in the organ as a first focal source location of the one or more focal source locations based on the unipolar electrogram classification result.

In some examples, the data structure may be defined as a residual convolutional neural network.

In some examples, the residual convolutional neural network may be defined using one-dimensional convolution filters.

In some examples, the plurality of layers of nodes may include 18 layers of nodes.

In some examples, the deep learning neural network classification model may be defined by training the data structure using raw unipolar electrogram data.

In some examples, the deep learning neural network classification model may be defined by training the data structure using augmented unipolar electrogram data.

In some examples, the augmented unipolar electrogram data may include multiple copies of the same raw unipolar electrogram data, where each copy has a different augmentation applied thereto.

In some examples, the augmented unipolar electrogram data may be generated by: normalizing the raw unipolar electrogram data; and at least one of baseline shifting the raw unipolar electrogram data using a constant noise signal; adding a Gaussian distribution of noise to the raw unipolar electrogram data; randomly cropping the raw unipolar electrogram data by replacing a segment of the raw unipolar electrogram data with zeros; or resampling the raw unipolar electrogram data.

In some examples, the computer readable instructions may be defined to configure the computer processor to identify the first location in the organ as a first focal source location by: comparing the unipolar electrogram classification result to a focal source identification threshold parameter; and identifying the first location in the organ as a first focal source location of the one or more focal source locations when the unipolar electrogram classification result meets or exceeds the focal source identification threshold parameter.

In some examples, the data structure may be configured to output the unipolar electrogram classification result as a probability value that the unipolar electrogram corresponds to a focal source location and the computer readable instructions may be defined to configure the computer processor to apply a focal source identification threshold parameter of at least 85%.

In some examples, the computer readable instructions may be defined to configure the computer processor to apply a focal source identification threshold parameter in a range between about 85%-95%.

In some examples, the computer readable instructions may be defined to configure the computer processor to apply a focal source identification threshold parameter of about 90%.

In some examples, the computer readable instructions may be defined to configure the computer processor to determine that the first electrical signal set is periodic by analyzing a bipolar electrogram in the first electrical signal set to identify periodicity in the bipolar electrogram.

In some examples, the computer readable instructions may be defined to configure the computer processor to analyze the bipolar electrogram to identify periodicity by determining that a peak spectral power of the bipolar electrogram satisfies a threshold power level.

In some examples, the computer readable instructions may be defined to configure the computer processor to determine that the peak spectral power of the bipolar electrogram satisfies the threshold power level by: determining a total spectral power of the bipolar electrogram; determining the peak spectral power; and determining that the peak spectral power is at least 10% of the total spectral power.

In some examples, the computer readable instructions may be defined to configure the computer processor to pre-process the bipolar electrogram prior to analyzing the bipolar electrogram to identify periodicity, where pre-processing the bipolar electrogram is defined to include: filtering the bipolar electrogram using a bandpass filter; rectifying the filtered bipolar electrogram; and calculating a fast Fourier transform of the rectified bipolar electrogram.

In some examples, the computer readable instructions may be defined to configure the computer processor to identify the unipolar electrogram as a periodic unipolar electrogram based on the presence of periodicity in the bipolar electrogram.

In some examples, the deep learning neural network classification model may be defined to generate the unipolar electrogram classification result using only the unipolar electrogram as an input from the first electrical signal set.

In some examples, the computer readable instructions may be defined to configure the computer processor to: receive a plurality of additional electrical signal sets, each of the additional electrical signal sets being obtained from different locations in the organ, and each of the additional electrical signal sets may include an additional unipolar electrogram; determine that a given additional electrical signal set is periodic; upon determining that the given additional electrical signal set is periodic, input the additional unipolar electrogram from that given additional electrical signal set to the data structure; receive an additional unipolar electrogram classification result as an additional output from the data structure; and identify an additional location in the organ that corresponds to the given additional electrical signal set as an additional focal source location of the one or more focal source locations based on the additional unipolar electrogram classification result.

In some examples, the organ may be a heart.

In some examples, the electrophysiological activity may be atrial fibrillation or ventricular fibrillation.

In some examples, the data structure may define the deep learning neural network classification model to detect the presence or absence of predominantly sustained, periodic unipolar QS complexes in the unipolar electrogram and to generate the unipolar electrogram classification result based on the detected presence or absence of the predominantly sustained, periodic unipolar QS complexes.

It will be appreciated by a person skilled in the art that a system, method or computer program product disclosed herein may embody any one or more of the features contained herein and that the features may be used in any particular combination or sub-combination. Other features and advantages of the present application will become apparent from the following detailed description taken together with the accompanying drawings. It should be understood, however, that the detailed description and the specific examples, while indicating preferred embodiments of the application, are given by way of illustration only, since various changes and modifications within the spirit and scope of the application will become apparent to those skilled in the art from this detailed description.

BRIEF DESCRIPTION OF THE DRAWINGS

For a better understanding of the various embodiments described herein, and to show more clearly how these various embodiments may be carried into effect, reference will be made, by way of example, to the accompanying drawings which show at least one example embodiment, and which are now briefly described.

Figure 1:
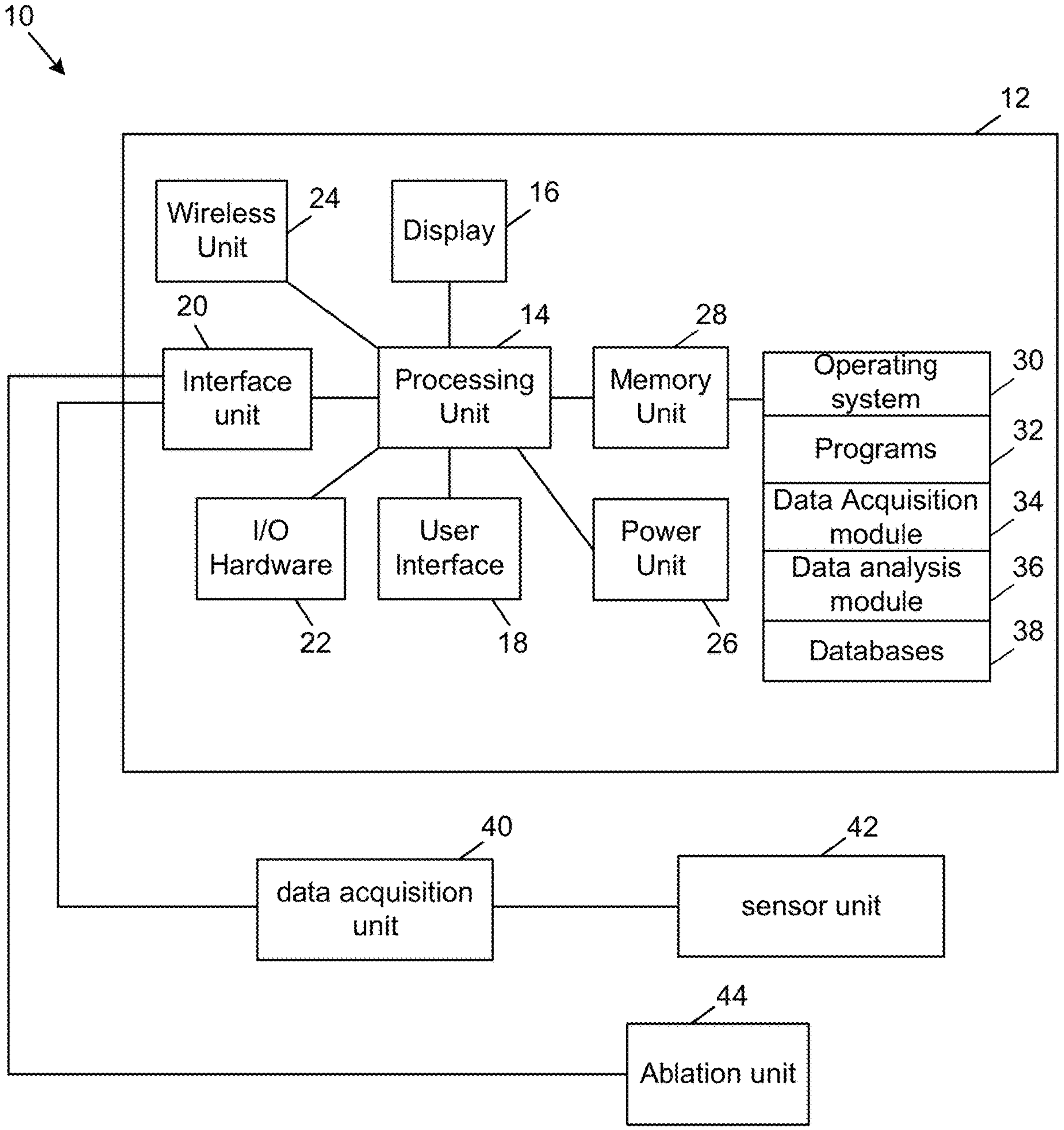
FIG. 1 is a block diagram of an example focal source identification system that can be used to identify focal source locations of electrophysiological activity for an organ.

Further aspects and features of the embodiments described herein will appear from the following description taken together with the accompanying drawings.

DETAILED DESCRIPTION OF THE EMBODIMENTS

Various apparatuses or methods will be described below to provide an example of an embodiment of the claimed subject matter. No embodiment described below limits any claimed subject matter and any claimed subject matter may cover methods or apparatuses that differ from those described below. The claimed subject matter is not limited to apparatuses or methods having all of the features of any one apparatus or methods described below or to features common to multiple or all of the apparatuses or methods described below. It is possible that an apparatus or methods described below is not an embodiment that is recited in any claimed subject matter. Any subject matter disclosed in an apparatus or methods described below that is not claimed in this document may be the subject matter of another protective instrument, for example, a continuing patent application, and the applicants, inventors or owners do not intend to abandon, disclaim or dedicate to the public any such invention by its disclosure in this document.

Furthermore, it will be appreciated that for simplicity and clarity of illustration, where considered appropriate, reference numerals may be repeated among the figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

It should also be noted that the terms "coupled" or "coupling" as used herein can have several different meanings depending in the context in which these terms are used. For example, the terms coupled or coupling can have a mechanical, electrical or communicative connotation. For example, as used herein, the terms coupled or coupling can indicate that two elements or devices can be directly connected to one another or connected to one another through one or more intermediate elements or devices via an electrical element, electrical signal or a mechanical element depending on the particular context. Furthermore, the term "communicative coupling" indicates that an element or device can electrically, optically, or wirelessly send data to another element or device as well as receive data from another element or device.

It should also be noted that, as used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

It should be noted that terms of degree such as "substantially", "about" and "approximately" as used herein mean a reasonable amount of deviation of the modified term such that the end result is not significantly changed. These terms of degree may also be construed as including a deviation of the modified term if this deviation would not negate the meaning of the term it modifies.

Furthermore, the recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about" which means a variation of up to a certain amount of the number to which reference is being made if the end result is not significantly changed.

The example embodiments of the systems and methods described in accordance with the teachings herein may be implemented as a combination of hardware or software. In some cases, the example embodiments described herein may be implemented, at least in part, by using one or more computer programs, executing on one or more programmable devices comprising at least one processing element, and a data storage element (including volatile and non-volatile memory and/or storage elements). These devices may also have at least one input device (e.g. a keyboard, mouse, a touchscreen, and the like), and at least one output device (e.g. a display screen, a printer, a wireless radio, and the like) depending on the nature of the device.

It should also be noted that there may be some elements that are used to implement at least part of one of the embodiments described herein that may be implemented via software that is written in a high-level procedural language such as object oriented programming. Accordingly, the program code may be written in C, $C^{++}$ or any other suitable programming language and may comprise modules or classes, as is known to those skilled in object oriented programming. Alternatively, or in addition thereto, some of these elements implemented via software may be written in assembly language, machine language or firmware as needed. In either case, the language may be a compiled or interpreted language.

At least some of these software programs may be stored on a storage media (e.g. a computer readable medium such as, but not limited to, ROM, magnetic disk, optical disc) or a device that is readable by a general or special purpose programmable device. The software program code, when read by the programmable device, configures the programmable device to operate in a new, specific and predefined manner in order to perform at least one of the methods described in accordance with the teachings herein.

Furthermore, at least some of the programs associated with the systems and methods of the embodiments described herein may be capable of being distributed in a computer program product comprising a computer readable medium that bears computer usable instructions for one or more processors. The medium may be provided in various forms, including non-transitory forms such as, but not limited to, one or more diskettes, compact disks, tapes, chips, and magnetic and electronic storage. In alternative embodiments, the medium may be transitory in nature such as, but not limited to, wire-line transmissions, satellite transmissions, internet transmissions (e.g. downloads), media, digital and analog signals, and the like. The computer useable instructions may also be in various formats, including compiled and non-compiled code.

The pathogenesis of atrial fibrillation (AF) is complex. In some cases, atrial fibrillation may develop as a result of localized drivers and abnormal atrial substrate outside the pulmonary veins (see for example Heijman J, Algalarrondo V, Voigt N, Melka J, Wehrens X H, Dobrev D, Nattel S. The value of basic research insights into atrial fibrillation mechanisms as a guide to therapeutic innovation: a critical analysis. Cardiovasc Res 2016 April 1; 109(4):467-79). This may account for the poor long-term success of pulmonary vein isolation (PVI) alone (see for example Ganesan A N, Shipp N J, Brooks A G, Kuklik P, Lau D H, Lim H S, Sullivan T, Roberts-Thomson K C, Sanders P. Long-term outcomes of catheter ablation of atrial fibrillation: a systematic review and meta-analysis. J Am Heart Assoc 2013 Mar. 18; 2(2): e004549). Using panoramic high-resolution mapping, localized drivers, including focal electrical sources have been observed to sustain experimental AF (see for example Lee S, Khrestian C M, Sahadevan J, Waldo A L. Reconsidering the multiple wavelet hypothesis of atrial fibrillation. Heart Rhythm 2020 November; 17(11):1976-83; and Lee S, Sahadevan J, Khrestian C M, Durand D M, Waldo A L. High density mapping of atrial fibrillation during vagal nerve stimulation in the canine heart: restudying the Moe hypothesis. J Cardiovasc Electrophysiol 2013 March; 24(3):328-35). However, their relevance in the pathogenesis of human AF is less clear. Detecting focal electrical sources in humans is challenging owing to the low spatial resolution of mapping techniques (see for example Roney C H, Cantwell C D, Bayer J D, Qureshi N A, Lim P B, Tweedy J H, Kanagaratnam P, Peters N S, Vigmond E J, Ng F S. Spatial Resolution Requirements for Accurate Identification of Drivers of Atrial Fibrillation. Circ Arrhythm Electrophysiol 2017 May; 10(5):e004899) and the complexity of electrogram (EGM) features (see for example DeBakker J M, Wittkampf F H. The pathophysiologic basis of fractionated and complex electrograms and the impact of recording techniques on their detection and interpretation. Ciro Arrhythm Electrophysiol 2010 April; 3(2):204-13).

To mitigate the risks of atrial fibrillation, focal electrical sources are often used as potential targets for atrial fibrillation (AF) catheter ablation. However, focal sources are time-consuming and challenging to identify. This is particularly the case when the unipolar electrograms (EGM) acquired from a patient are numerous and complex.

Embodiments described herein provide systems, methods, devices and computer program products that can automatically identify focal source locations. In addition, the systems, methods, devices and computer program products may be configured to guide ablation of the focal source locations so identified. Automatically (and accurately) identifying focal source locations may dramatically improve the results of catheter ablation for the treatment of atrial fibrillation. Automated detection may also minimize the potential for human error in the focal source identification process and improve the reliability in focal source identification among multiple users.

Embodiments described herein may use deep learning (DL) neural network models with raw unipolar EGMs as inputs in order to automate detection of putative focal sources. In particular, embodiments described wherein may provide a neural network classification model defined to automate detection of unipolar EGM signal features that are associated with focal sources, such as but not limited to sustained, periodic QS complexes (see, for example, Lee S, Sahadevan J, Khrestian C M, Cakulev I, Markowitz A, Waldo A L. Simultaneous Biatrial High-Density (510-512 Electrodes) Epicardial Mapping of Persistent and Long-Standing Persistent Atrial Fibrillation in Patients: New Insights Into the Mechanism of Its Maintenance. Circulation 2015 Dec. 1; 132(22):2108-17). Electrical signal sets can be received from one or more locations in a patient. The raw unipolar electrograms from these electrical signal sets can be input to the neural network model in order to classify the corresponding locations as focal source locations or non-focal source locations.

In some cases, the electrical signal sets may be pre-processed to detect the presence of periodicity prior to inputting the raw unipolar electrograms to the neural network model. This may facilitate the focal source detection performed by the neural network model.

The neural network models described herein to provide automated detection of focal source locations may be defined using a residual convolutional neural network. The residual convolutional neural network can be trained to discriminate between unipolar electrograms corresponding to focal source locations and unipolar electrograms corresponding to non-focal source locations.

A number of existing residual neural networks have been developed to perform computer vision and image recognition operations. In embodiments described herein, a residual convolutional neural network structure is provided that is specifically configured for analysis of electrogram signal data.

In some examples, the neural network model may be defined using a neural network that includes 18 node layers. For example, the neural network may be arranged into a data structure that is a modified form of a Resnet18 network. The neural network data structure can be specifically configured to analyze electrogram signal data. The residual convolutional neural network used in embodiments described herein can be trained to discriminate between electrogram signal data indicating a focal source (also referred to as a Focal Source and Trigger or a FaST) and electrogram signal data indicating a non-focal source (e.g. non-FaST electrogram signal data).

The inventors tested an example implementation of the embodiments described herein using electrogram data acquired from a cohort of patients who experienced atrial fibrillation. The example implementation was trained using raw unipolar electrogram data from a first subset of the patients. This implementation was then tested on raw unipolar electrogram data from a second subset of the patients. Testing of the example implementation showed automated and accurate classification of electrogram signal data corresponding to focal source locations. In particular, the performance of the example implementation was shown to be similar to the re-classification of focal source locations by cardiologists. The results indicate that implementations of the embodiments described herein to identify focal source locations may improve the efficiency of real-time focal source detection, and in particular focal source detection that can be used for (and in some cases to guide) targeted AF ablation therapy.

Referring now to FIG. 1, shown therein is a block diagram of an example embodiment of a focal source identification system 10 that can be used to identify one or more focal source locations of electrophysiological activity for an organ. The system 10 includes an operator unit 12, a data acquisition unit 40, a sensor unit 42, and an ablation unit 44. The system 10 is provided as an example and there can be other embodiments of the system 10 with different components or a different configuration of the components described herein. The system 10 further includes several power supplies (not all shown) connected to various components of the system 10 for providing power thereto as is commonly known to those skilled in the art. In general, a user may interact with the operator unit 12 to record electrical signal sets, such as bipolar and unipolar EGM data from a subject or a patient, and then perform data analysis on the recorded data to identify focal source locations of electrophysiological activity for an organ of the patient.

The operator unit 12 comprises a processing unit 14, a display 16, a user interface 18, an interface unit 20, Input/Output (I/O) hardware 22, a wireless unit 24, a power unit 26 and a memory unit 28. The memory unit 28 comprises software code for implementing an operating system 30, various programs 32, a data acquisition module 34, a data analysis module 36, and one or more databases 38. Many components of the operator unit 12 can be implemented using a desktop computer, a laptop, a mobile device, a tablet, and the like.

The processing unit 14 controls the operation of the operator unit 12 and can be any suitable processor, controller or digital signal processor that can provide sufficient processing power depending on the configuration, purposes and requirements of the system 10 as is known by those skilled in the art. For example, the processing unit 14 may be a high performance general processor. In alternative embodiments, the processing unit 14 may include more than one processor with each processor being configured to perform different dedicated tasks. In alternative embodiments, specialized hardware can be used to provide some of the functions provided by the processing unit 14.

The display 16 can be any suitable display that provides visual information depending on the configuration of the operator unit 12. For instance, the display 16 can be a cathode ray tube, a flat-screen monitor and the like if the operator unit 12 is a desktop computer. In other cases, the display 16 can be a display suitable for a laptop, tablet or handheld device such as an LCD-based display and the like. The display 16 may display various graphical user interfaces to a user of the operator unit 12, such as a results interface displaying or otherwise indicating the focal source locations identified by the methods described herein.

The user interface 18 can include at least one of a mouse, a keyboard, a touch screen, a thumbwheel, a track-pad, a track-ball, a card-reader, voice recognition software and the like again depending on the particular implementation of the operator unit 12. In some cases, some of these components can be integrated with one another.

The interface unit 20 can be any interface that allows the operator unit 12 to communicate with other devices or computers. In some cases, the interface unit 20 can include at least one of a serial port, a parallel port or a USB port that provides USB connectivity. The interface unit 20 can also include at least one of an Internet, Local Area Network (LAN), Ethernet, Firewire, modem or digital subscriber line connection. Various combinations of these elements can be incorporated within the interface unit 20.

The I/O hardware 22 is optional and can include, but is not limited to, at least one of a microphone, a speaker and a printer, for example.

The wireless unit 24 is optional and can be a radio that communicates utilizing CDMA, GSM, GPRS or Bluetooth protocol according to standards such as IEEE 802.11a, 802.11b, 802.11g, or 802.11n. The wireless unit 24 can be used by the operator unit 12 to communicate with other devices or computers.

The power unit 26 can be any suitable power source that provides power to the operator unit 12 such as a power adaptor or a rechargeable battery pack depending on the implementation of the operator unit 12 as is known by those skilled in the art.

The memory unit 28 can include RAM, ROM, one or more hard drives, one or more flash drives or some other suitable data storage elements such as disk drives, etc. The memory unit 28 may be used to store an operating system 30 and programs 32 as is commonly known by those skilled in the art. For instance, the operating system 30 provides various basic operational processes for the operator unit 12. The programs 32 include various user programs so that a user can interact with the operator unit 12 to perform various functions such as, but not limited to, acquiring data, viewing and manipulating data, adjusting parameters for data analysis, reviewing identified focal source locations, guiding catheter ablation and so on.

The data acquisition module 34 is used to obtain electrical signal sets from one or more locations in a patient or a subject, and more particularly from one or more locations at an organ of interest for the patient or subject. For example, in some embodiments, the data acquisition module 34 is operable to acquire signals from at least one region in the atrium or ventricle of a patient's heart. The data acquisition module 34 is coupled to the data acquisition unit 40 and the sensor unit 42 in order to acquire these signals.

In some cases, the data acquisition module 34 may be used to obtain electrical signal sets from a single location at an organ of interest. In other cases, the data acquisition module 34 may be used to obtain electrical signal sets from multiple locations simultaneously depending on the sensor unit 42 that is used. For example, in order to obtain electrical signal sets from multiple locations simultaneously, the data acquisition unit 40 may use a sensor unit 42 having a multi-electrode catheter.

Each electrical signal set obtained by the data acquisition module 34 can include bipolar and unipolar EGM from a region of electrically active tissue, such as the atrium or ventricle of a patient's heart, for example. In some cases, the electrical signal sets may also include the surface ECG lead signals obtained from the patient. The electrical signal sets may be preprocessed by the data acquisition unit 40 and transferred to the operator unit 12 through interface unit 20. The preprocessing that is done may include standard signal processing techniques such as, but not limited to, at least one of amplification, filtering and de-noising (e.g. averaging) using parameters that depend on the particular signals that are acquired. The interface unit 20 may be a multichannel data interface coupling the data acquisition unit 40 to the operator unit 12.

It should be noted that while the system 10 is described as having the data acquisition unit 40, the sensor unit 42 and the data acquisition module 34 for acquiring electrophysiological signals, the system 10 may be implemented without these components in an alternative embodiment. This may be the case, for instance where the electrophysiological signals have already been recorded and the system 10 is being used to analyze the recorded electrophysiological signals.

Each electrical signal set received by the system 10 can be associated with a particular location in a patient's organ. The particular location can identify the specific portion of the organ from which that electrical signal set was acquired. The electrical signal set may be associated with the particular location in various ways. For instance, the electrical signal set may include coordinate data identifying the corresponding location from which that electrical signal set was acquired. Alternately or in addition, the electrical signal set may have an associated set identifier and the set identifier may be associated with the corresponding location (e.g. stored in a file on database 38).

The data analysis module 36 processes the data that is recorded by the data acquisition module 34 in order to determine focal source locations of electrophysiological activity for an organ of interest. For example, the electrophysiological activity may be atrial fibrillation or ventricular fibrillation of a patient's heart. Example embodiments of analysis methods that may be employed by the data analysis module 36 are described in more detail with respect to FIGS. 3 and 4. In addition, an example architecture of a neural network that may be used to implement aspects of the data analysis module 36 is shown in FIG. 5. For example, the neural network architecture may be used to define a data structure that can classify a unipolar electrogram signal as corresponding to a focal source location or a non-focal source location.

The focal source locations may then be provided as an output consisting of an electronic file or a display image with information in the form of a focal source classification result, a list of focal sources, a cardiac map and the like. The data analysis module 36 may be coupled to additional systems that can be used to interpret and/or display the focal source location data. For example, the data analysis module 36 can be coupled to a commercially available mapping system, such as the CARTO™ system manufactured by Biosense Webster, or the NAVX™ system manufactured by St. Jude Medical, to mark locations in the atrium or ventricle of a patient that have been identified as focal source locations. Alternatively, the data analysis module 36 may be coupled to a memory element, such as the databases 38 or a storage element, for analyzing previously recorded electrophysiological signals and/or to store the results of focal source classifications.

In alternative embodiments, the modules 34 and 36 may be combined or may be separated into further modules. The modules 34 and 36 are typically implemented using software, but there may be instances in which they are implemented using FPGA, application specific circuitry or neuromorphic hardware for example. For ease of understanding, certain aspects of the methods described in accordance with the teachings herein are described as being performed by the data analysis module 36. It should be noted, however that these methods are not limited in that respect, and the various aspects of the methods described in accordance with the teachings herein may be performed by other modules for identifying focal source locations.

The databases 38 can be used to store data for the system 10 such as system settings, parameter values, calibration data, training data and so on. The databases 38 can also store other information required for the operation of the programs 32 or the operating system 30 such as dynamically linked libraries and the like.

The databases 38 may also store a data structure that can be used to define a deep learning neural network classification model configured to generate a unipolar electrogram classification result. For instance, the data structure may be implemented using a plurality of nodes (e.g. artificial neurons). Each node may have an associated node input and node output. The plurality of nodes can be arranged into a plurality of layers of nodes including at least one input layer and at least one output layer. The data structure may be trained to define the connections (e.g. weightings) between the nodes and/or layers in order to provide a classification model configured to generate a unipolar electrogram classification result. An example neural network structure that may be stored as a data structure in the database 38 is described in further detail herein below with reference to FIG. 4.

The operator unit 12 comprises at least one interface that the processing unit 14 communicates with in order to receive or send information. This interface can be the user interface 18, the interface unit 20 or the wireless unit 24. For instance, threshold parameters such as the parameters used by the system 10 in order to identify a focal source location and/or signal periodicity may be inputted by a user through the user interface 18 or they may be received through the interface unit 20 from a computing device. The processing unit 14 can communicate with either one of these interfaces as well as the display 16 or the I/O hardware 22 in order to output information related to focal source location, neural network model classification results and threshold parameters for example. In addition, users of the operator unit 12 can communicate information across a network connection to a remote system for storage and/or further analysis in some embodiments. This communication may also include email communication.

The user can also use the operator unit 12 to input information needed for system parameters that are needed for proper operation of the system 10 such as calibration information and other system operating parameters as is known by those skilled in the art. Data that are obtained from tests, as well as parameters used for operation of the system 10, may be stored in the memory unit 28. The stored data may include raw recorded data, preprocessed recorded data as well as result data such as focal source classification results, focal source location data, processed cardiac map data and the like.

The data acquisition unit 40 comprises hardware and circuitry that is used to record electrical signal sets from a patient or subject. The data acquisition unit 40 may be custom designed or may be implemented using commercially available clinical electrophysiology data acquisition systems and/or three-dimensional electro-anatomical mapping systems such as, but not limited to, the CARTO™ system manufactured by Biosense Webster, or the NAVX™ system manufactured by St. Jude Medical, for example.

The sensor unit 42 is used to measure the electrical information from the organ of the patient or subject. The sensor unit 42 may have one or only a few electrodes such as a roving 4-electrode catheter, for example. In other embodiments, the sensor unit 42 can be a multi-electrode sensor such as a 10- or 20-electrode catheter such as the Lasso™ (Biosense Webster), the Pentarray™ (Biosense Webster) and the Spiral™ (St. Jude Medical) that can be used to gather electrical information from discrete areas of the organ. In other embodiments, a multi-electrode contact basket catheter can also be used such as the Constellation™ (Boston Scientific).

The ablation unit 44 is used to ablate focal source locations that have been identified in the patient's organ of interest. The ablation unit 44 can be any suitable ablation unit such as the commercially available Stockert™ ablation generator manufactured by Biosense Webster, for example. The ablation unit 44 may be used to deliver heat energy to the atrium of the patient at identified ablation targets. For example, a medical practitioner may use the methods described in accordance with the teachings herein to identify focal source locations for ablation and to guide ablation of those focal source locations.

Figure 2B:
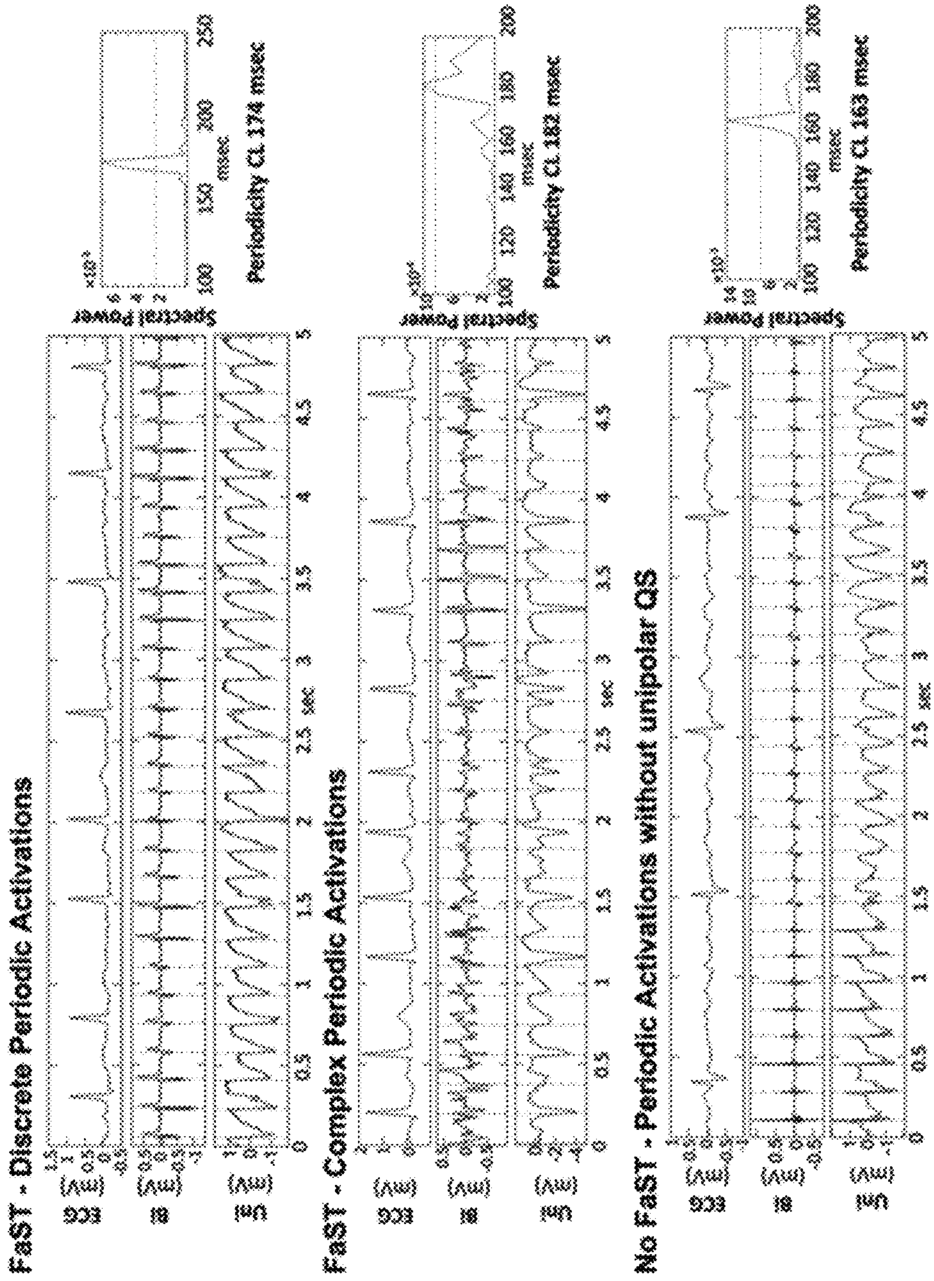
FIG. 2B illustrates example plots of a unipolar electrogram, a bipolar electrogram and an ECG lead V1 received from recording sites in patients.
Figure 2A:
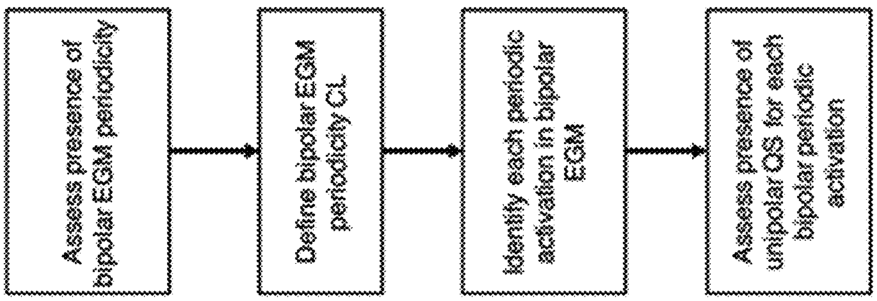
FIG. 2A illustrates a flowchart of a focal source identification method for analyzing electrophysiological activity from an organ to locate a focal source of electrical activity for the organ.

Referring now to FIG. 2A, shown therein is an example process for focal source detection in which bipolar and unipolar EGMs are analyzed for periodicity and unipolar QS features are used as footprints of centrifugal wave propagation (see for example Gizurarson S, Dalvi R, Das M, Ha A C T, Suszko A, Chauhan V S. Hierarchical Schema for Identifying Focal Electrical Sources During Human Atrial Fibrillation: Implications for Catheter-Based Atrial Substrate Ablation. JACC Clin Electrophysiol 2016 November; 2(6):656-66; and Kochhauser S, Verma A, Dalvi R, Suszko A, Alipour P, Sanders P, Champagne J, Macle L, Nair G M, Calkins H, Wilber D J, Chauhan V S. Spatial Relationships of Complex Fractionated Atrial Electrograms and Continuous Electrical Activity to Focal Electrical Sources: Implications for Substrate Ablation in Human Atrial Fibrillation. JACC Clin Electrophysiol 2017 November; 3(11):1220-8). As shown in FIG. 2A, the periodicity of a bipolar EGM is assessed and then the periodicity cycle length (CL) is identified. For bipolar EGMs demonstrating periodicity within a specified CL ranging from 100 to 250 ms (i.e. a physiologic atrial refractory period), local bipolar periodic activations were annotated using a graph search function. For this purpose, candidate local activations were automatically selected provided their amplitude was above a noise threshold of 0.05 mV and a slew rate >0.014 mV/ms. Local periodic activations across the 5-second bipolar EGM were identified as those with the greatest number of consecutive candidate activations having the extracted periodicity CL, which satisfied the lowest cost of a matrix containing the difference between each candidate activation and the extracted periodicity CL. This ensured that sustained periodic activations with predefined periodicity CL were identified regardless of their EGM amplitude, which itself is not a pre-requisite for defining local activation. These local periodic bipolar activations were then transposed to the corresponding unipolar EGMs in order to annotate unipolar EGM onset and thereby facilitate classification of unipolar morphology as QS or non-QS. A focal source was defined based on the presence of sustained bipolar EGM periodicity and a dominant unipolar QS pattern (i.e. R/S ratio <0.1) in >90% of EGMs over a 5-second recording. This was typically assigned manually by 2 cardiologists in real-time before ablation. Any disagreement in focal source classification by the cardiologists was generally resolved by consensus. Focal source locations were classified as pulmonary vein (PV) vs. extraPV and they were considered to be anatomically distinct if >7 mm from one another.

In the example process shown in FIG. 2A for identifying focal source locations, the accurate detection of sustained, periodic unipolar QS electrograms is critical and requires over reading by a cardiologist after the onset of the unipolar electrograms have been identified and annotated. However, this can be challenging when unipolar EGMs appear fractionated and non-stationary over 5-s recordings. Furthermore, this process requires manual analysis by a cardiologist to detect the presence of a focal source.

The use of deep learning techniques to classify raw electrogram signals relating to atrial fibrillation has not previously been explored. However, the inventors identified that deep learning neural network models may be particularly advantageous for identifying focal source locations as these models can be designed to learn and identify features from raw input signals without requiring manual features engineering or identification to be performed in advance. Accordingly, the inventors developed systems and methods for automating the detection of sustained, periodic unipolar QS EGMs using a deep learning neural network structure that can improve the reliability and efficiency of focal source location detection for cardiologists performing AF driver catheter ablation. In particular, a deep learning neural network model was developed and trained on raw unipolar EGMs to allow automated and accurate identification of focal source locations during AF. These focal source locations can be identified as putative focal source targets for ablation, and in some cases may be used to guide catheter ablation of the putative focal source targets.

Figure 3:
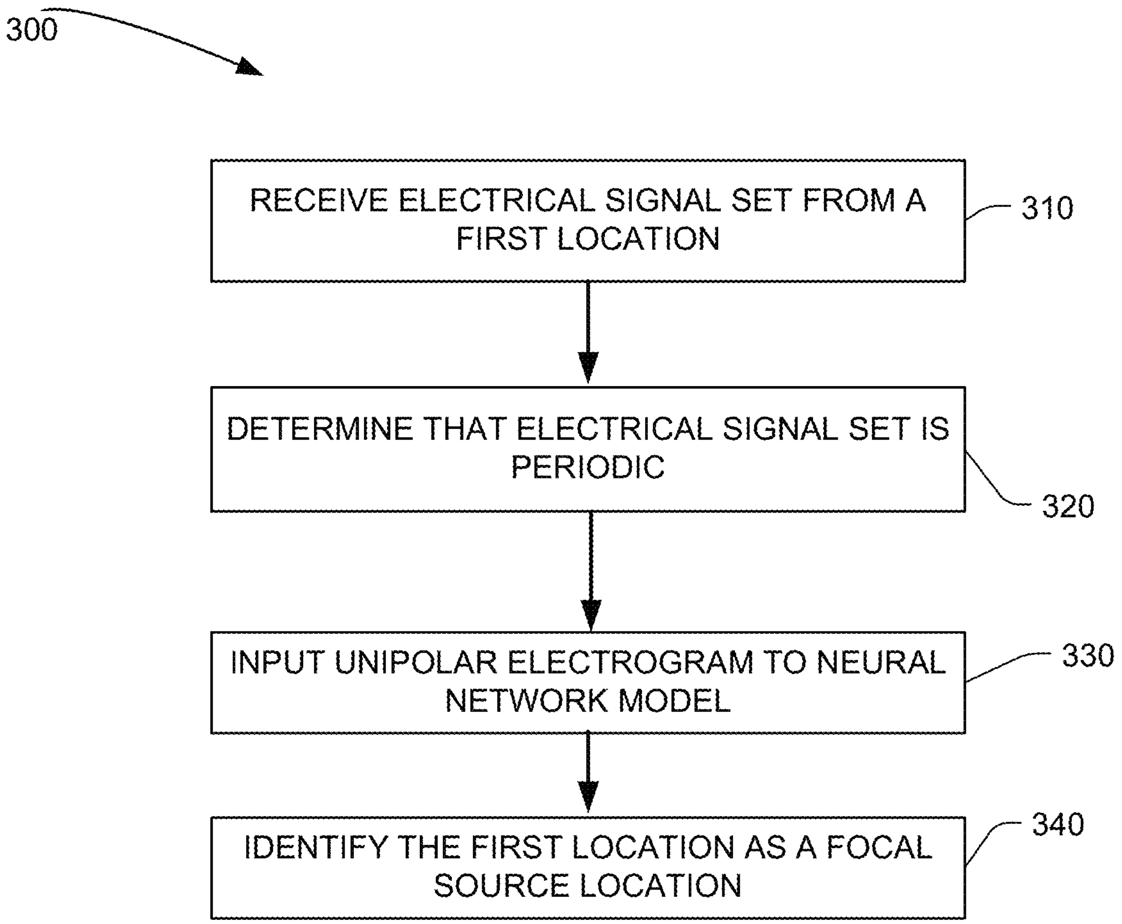
FIG. 3 is a flowchart of an example embodiment of an automated focal source identification method for analyzing electrophysiological activity from an organ to locate a focal source of electrical activity for the organ.

Referring now to FIG. 3, shown therein is an example method 300 that may be used to automatically identify one or more focal source locations of electrophysiological activity for an organ. The example method 300 shown in FIG. 3 may be implemented using various signal analysis and signal acquisition systems such as the system 10 shown in FIG. 1. The example method 300 may be performed using a deep learning neural network classification model that is defined using a neural network structures such as the example neural network architecture shown in FIG. 4 and described herein below.

At 310, a first electrical signal set corresponding to (and obtained from) a first location of the organ can be received. The electrical signal set may be recorded at the first location using the data acquisition unit 40 and the sensor unit 42, it may be retrieved from a storage element or it may be received from another computing device that may be at a remote location, for example. In some cases, a plurality of additional electrical signal sets may also be obtained with each of the additional electrical signal sets being recorded from different locations in the organ.

In some cases, the plurality of electrical signal sets may be recorded individually at separate times. In other cases, the plurality of electrical signal sets, or subsets of the electrical signal sets may be recorded simultaneously. For example, 10 electrical signals sets may be recorded simultaneously using a sensor unit 42 with a multi-electrode catheter having 10 sensors or a catheter having one sensor may be positioned over time at 10 different locations to obtain the 10 electrical signal sets.

The first electrical signal set generally includes a unipolar EGM corresponding to the electrical signals obtained from the first location. The first electrical signal set can also include a bipolar EGM corresponding to the electrical signals obtained from the first location. The unipolar EGM and the bipolar EGM may be recorded for various lengths of time as long as the recording time frame is long enough so that enough data suitable for analysis is recorded. In some embodiments where the electrical signal sets are being recorded in real-time, the recording time frame may be selected by a user of the operator unit 12.

In some examples, the electrical signal sets used to train the deep learning neural network classification model may use a specified recording time frame. This may simplify the neural network structure and training. In such cases, the electrical signal sets received at 310 may also be recorded using the same specified recording time frame.

At 320, the first electrical signal set is analyzed to determine whether the first electrical signal set is periodic. As noted at 310, the first electrical signal set can include a bipolar electrogram. The first electrical signal set may be determined to be periodic by identifying periodicity in the bipolar electrogram.

Periodicity may be identified in the bipolar electrogram in various ways. For example, the bipolar electrogram may be analyzed to determine whether a peak spectral power of the bipolar electrogram satisfies a threshold power level. If the peak spectral power satisfies the threshold power level, the bipolar electrogram may be identified as having periodicity.

In some cases, the threshold power level may be defined as a threshold percentage of the overall spectral power. For example, a total spectral power of the bipolar electrogram may be identified. The spectral frequency with the peak spectral power can also be identified. The first electrical signal set may be identified as periodic by determining that the peak spectral power is at least a threshold percentage (e.g. 10%) of the total spectral power. Thus, periodicity may be determined to be present if the spectral frequency with the largest spectral power contains at least 10% of the total spectral power.

The bipolar electrogram can be pre-processed prior to determining whether the bipolar electrogram has a periodicity. The pre-processing may include filtering the bipolar electrogram using a bandpass filter. For example, the bipolar electrogram may be filtered using a first bandpass filter (e.g. with a filter stopband of 40-250 Hz) and then a second bandpass filter (e.g. with a filter stopband of 0.5-20 Hz). Following filtering, the filtered bipolar electrogram may be rectified. A fast Fourier transform of the rectified bipolar electrogram may then be calculated. The pre-processed bipolar electrogram may then be analyzed to determine whether periodicity is present.

At 330, the unipolar electrogram may be input to a deep learning neural network classification model. The deep learning neural network classification model may be configured to generate a unipolar electrogram classification result in response to receiving the unipolar electrogram as an input.

In some cases, the unipolar electrogram may be input to the deep learning neural network classification model only upon determining at 320 that the first electrical signal set is periodic. Determining that the first electrical signal set is periodic may, in effect, involve determining that the unipolar electrogram is periodic. As indicated above at 320, unipolar electrogram periodicity may be determined based on the presence of periodicity in the corresponding bipolar electrogram. That is, the unipolar electrogram may be identified as a periodic unipolar electrogram (or not) based on the presence (or absence) of periodicity in the corresponding bipolar electrogram (i.e. the bipolar electrogram from the same electrical signal set—that is, the bipolar electrogram acquired from the same location and at the same time as the unipolar electrogram). Electrical signal sets that are not periodic may be omitted from evaluation by the deep learning neural network classification model. In some cases, only the unipolar electrogram may be input to the classification model without necessarily inputting the corresponding periodic bipolar electrogram. Intraoperative mapping studies in patients with atrial fibrillation have found that periodic unipolar electrograms with QS morphology are typically recorded at focal source locations where centrifugal wave propagation is also demonstrated (see, for example, Lee S, Sahadevan J, Khrestian C M, Cakulev I, Markowitz A, Waldo A L. Simultaneous Biatrial High-Density (510-512 Electrodes) Epicardial Mapping of Persistent and Long-Standing Persistent Atrial Fibrillation in Patients: New Insights Into the Mechanism of Its Maintenance. Circulation 2015 Dec. 1; 132(22):2108-17). Accordingly, the inventors have identified that inputting the periodic unipolar electrogram without inputting the corresponding periodic bipolar electrogram into the deep learning neural network model may increase the specificity of focal source detection compared to inputting nonselected unipolar electrograms.

In some cases, the entire unipolar electrogram may be input to the classification model. The unipolar electrogram may be input to the classification model without any initial analysis thereof. That is, the unipolar electrogram may be input to the classification model without any analysis of the number of dominant periodicities, the locations of periodic activations or peaks, and so forth. Rather, the electrical signal set may be identified as having a dominant periodicity and then the entire unipolar electrogram can be input to the classification model once periodicity is detected at 320.

In some examples, the unipolar electrogram may be normalized before being input to the classification model. This may provide consistency in the inputs to the model, which may improve overall model accuracy. For example, the magnitude of the unipolar electrogram may be normalized using a min-max feature scaling normalization. Alternately or in addition, the unipolar electrogram may be down-sampled to a specified frequency. For example, the unipolar electrogram may be down-sampled to 200 Hz using a fast Fourier transformation.

The deep learning neural network classification model can be defined using a data structure that includes a plurality of nodes. Each of the nodes can have an associated node input and node output. The plurality of nodes can be arranged into a plurality of layers of nodes. The data structure may be defined as an artificial neural network. For example, the artificial neural network may be defined with 18 layers of neural nodes. Each of the nodes in the data structure may correspond to an artificial neuron within that artificial neural network.

Each node may have an associated node response function. The node response function for a given node may be defined to receive an input at the node input of that node and produce a corresponding output at the node output of that node.

Figure 4:
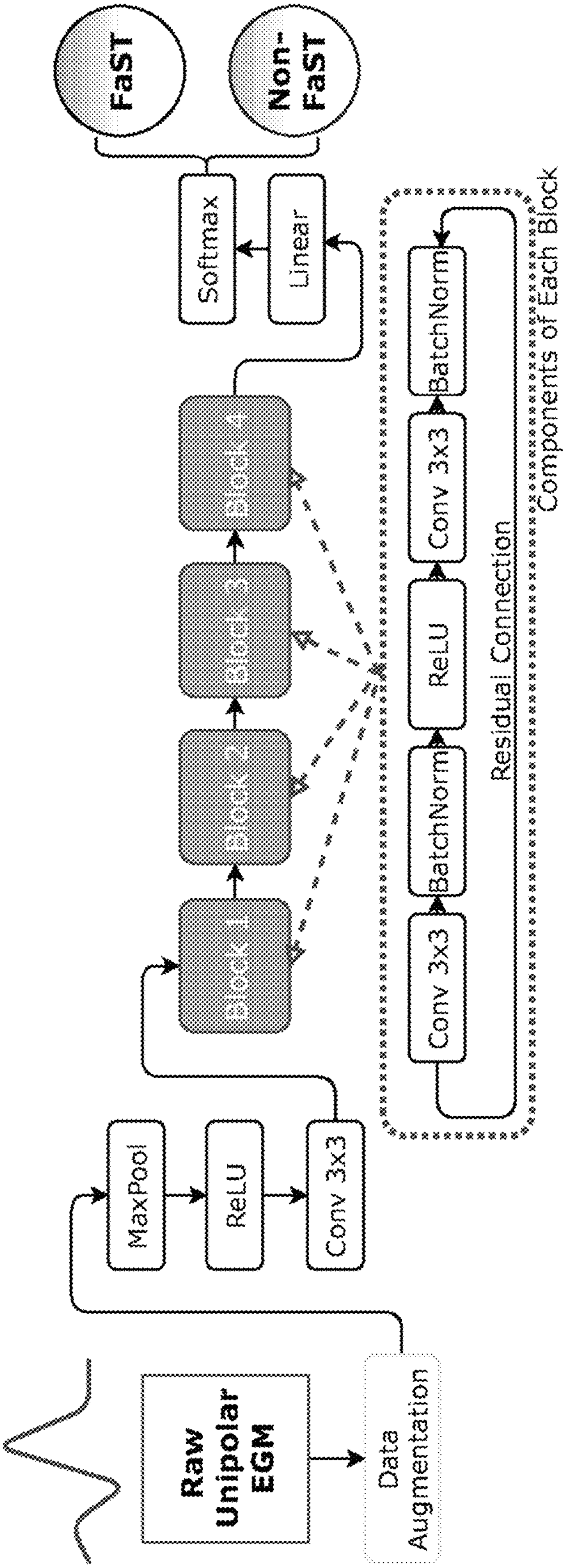
FIG. 4 is a block diagram of an example neural network architecture that may be used in the system of FIG. 1 to identify focal source locations of electrophysiological activity for an organ.
Figure 5:
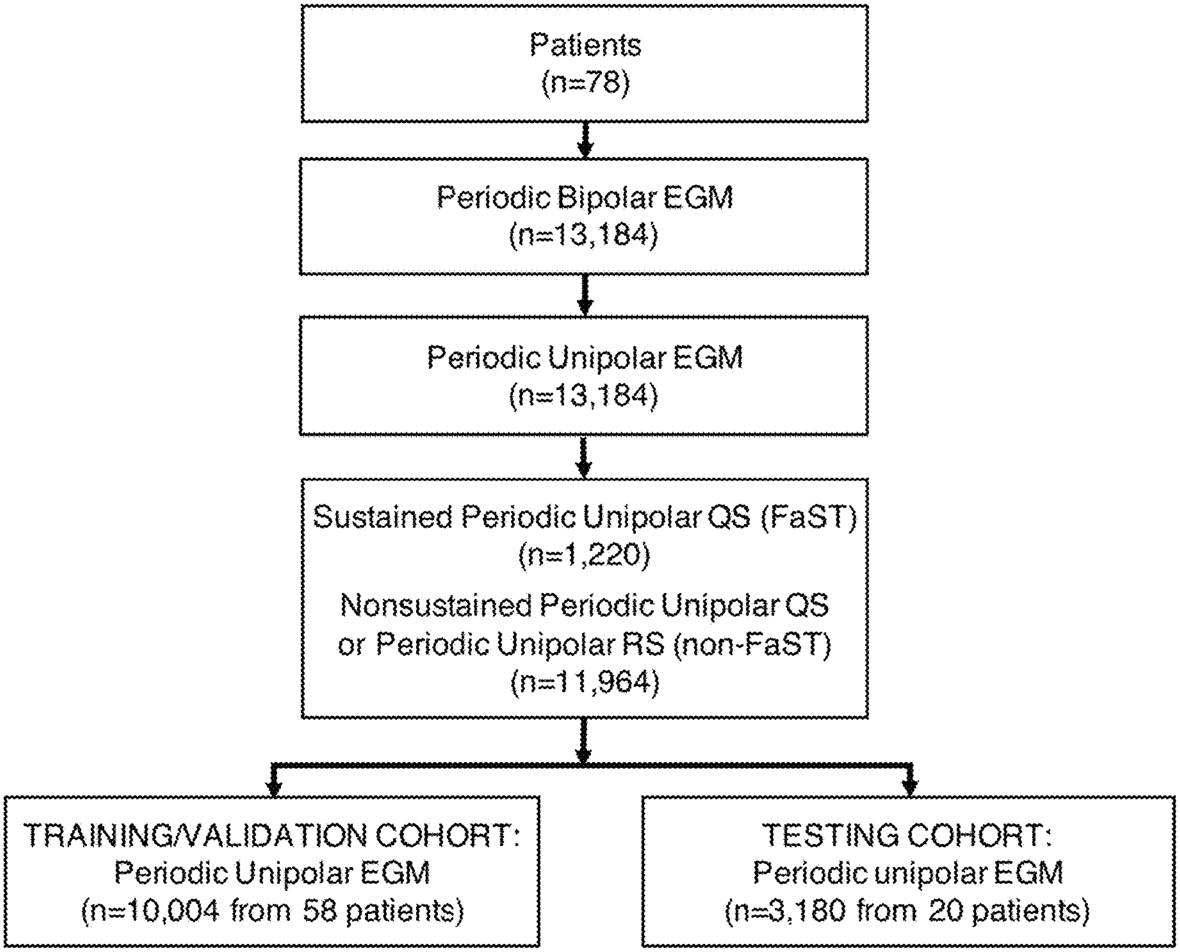
FIG. 5 is a flowchart illustrating the division of patients and recorded electrograms into training and testing cohorts that were used with an example implementation of the example neural network architecture of FIG. 4 to generate testing results shown and described herein.

FIG. 4 illustrates an example of the neural network structure that may be used to define the deep learning neural network classification model. As shown in FIG. 4, the deep learning neural network classification model may be defined using a residual convolutional neural network.

The residual convolutional neural network can be defined to receive a unipolar electrogram as an input and output a classification result indicating whether or not the unipolar electrogram corresponds to a focal source location or a non-focal source location.

The example illustrated in FIG. 4 is a deep neural network structure partially inspired by the architecture used in ResNet-18 for image recognition. However, the original ResNet-18 structure was designed for image analysis involving two-dimensional inputs and cannot be applied to unipolar electrograms analysis. The inventors have modified the original ResNet-18 structure in order to adapt the model for analysis and classification of unipolar electrograms.

In some examples, the residual convolutional neural network may be implemented as an 18-layer neural network. The residual convolutional neural network can include multiple blocks and include a convolutional layer, a pooling (e.g. the MaxPool one-dimensional max pooling layer), a batch normalization, a dropout, a nonlinear activation and a residual connection.

As illustrated, the neural network can include four residual convolutional blocks and one fully connected node layer. In the example illustrated, each residual convolutional block consists of two convolutional layers (in the example illustrated, a convolutional layer with a kernel size of 3 is shown), two batch normalization layers (BatchNorm) and one non-linear activation layer (ReLU). In the convolutional layer of each block, the convolutional filters are defined as one-dimensional kernel filters specifically adapted for analysis of unipolar electrograms. This modification allows the neural network structure to analyze unipolar electrograms. The size of network can be trimmed by reducing the number of channels for each block to, 16, 32, 64 and 128 respectively.

In the example residual convolutional neural network illustrated, each convolutional block receives an input in a first dimensional space and abstracts the features from that input into a higher level (e.g. a higher dimensional) representation. The convolutional blocks can be configured to abstract features gradually from raw inputs (of the raw unipolar electrogram) to a higher-level representation.

The residual convolutional neural network model may be implemented as a one-dimensional (1-D) residual, convolutional, deep neural network (CNN) through PyTorch. The deep learning classification model can be defined using the same hyper-parameter settings as ResNet-18, such as kernel size, stride size and dropout rate (see for example He K, Zhang X, Ren S, Sun J. Identity mappings in deep residual networks. European conference on computer vision 2016; (October 8):630-45).

The neural network structure may be implemented using a variety of hyper-parameters. To prevent model overfitting, a subset of hyper-parameters for model training can be searched including the kernel size (e.g. 1, 3, 5 etc.), dropout rate (e.g. 0.1, 0.5, 0.8 etc.), batch size (e.g. 16, 32, 64 etc.), initial learning rate (e.g. 0.001, 0.003, 0.01, 0.03 etc.) and the learning rate scheduler (e.g. constant, linear decay etc.). The best hyper-parameter combination can be identified that the combination providing the best performance in validation and can be determined found through a grid search with a 3-fold cross-validation. To train the neural network model for testing, the best searched hyper-parameters can be applied to the whole training cohort to train the neural network model.

The hyper-parameters may be tuned during training of the neural network model. An initial set of hyper-parameters may be selected. For instance, default values of hyper-parameters may be selected for the initial set. The neural network model can then be trained and tested using the initial set of hyper-parameters. At least one additional set of hyper-parameters may also be selected. Each set of hyper-parameters can include a unique combination of hyper-parameters values (typically with slight deviations between the sets). The training and testing of the neural network model can then be repeated for each additional set of hyper-parameters. The hyper-parameter values used with the neural network model can be selected as the set of hyper-parameters that provided the best validation results during testing of the neural network model.

The residual convolutional neural network can be trained to generate a unipolar electrogram classification result in response to receiving the unipolar electrogram as an input. Training the model can be used to determine connection weights between the plurality of nodes in the artificial neural network that enable the neural network to generate a unipolar electrogram classification result when a unipolar electrogram is received at the input layer of the artificial neural network. Each connection weight is coupled to at least one of a corresponding node input or a corresponding node output. Each connection weight can be configured to be multiplied by at least one of the input received by the corresponding node input or the output produced by the corresponding node output.

In some examples, the deep learning neural network classification model may be trained using raw unipolar electrogram data. The raw unipolar electrogram data may be normalized prior to training. Alternately or in addition, the deep learning neural network classification model may be trained using augmented unipolar electrogram data. This may improve the generalizability of the classification mode. For example, augmenting the unipolar electrograms may involve adding artificial noise to the unipolar electrograms. Augmenting the unipolar electrograms can be used to increase the size of training dataset by adding new unipolar electrogram examples with artificial noise. This may help prevent overfitting of the classification model.

In some examples, training the deep learning neural network classification model using augmented unipolar electrogram may involve generating multiple copies of the same unipolar electrogram. Each copy may be varied with a different augmentation applied thereto. One or more of the augmented copies and/or the raw unipolar electrogram may be provided as inputs to the neural network for training.

Figure 9:
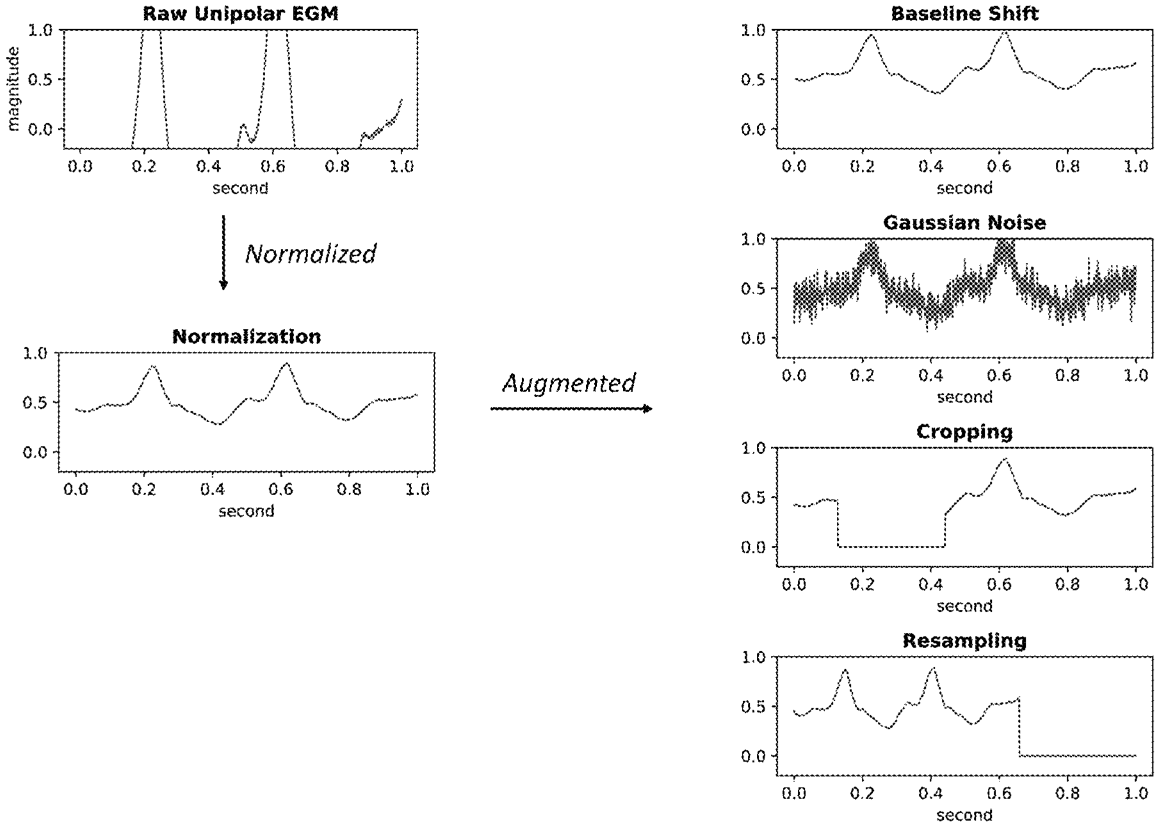
FIG. 9 illustrates example plots of a raw unipolar electrogram and associated normalized and augmented electrogram signal sets in accordance with an example embodiment.

Referring to FIG. 9, shown therein are examples of signal normalization and artificial data augmentations that may be used to train the deep learning neural network classification model. As shown in the example of FIG. 9, the data augmentations may include one or more of baseline shifting, Gaussian noise, cropping and resampling.

A unipolar electrogram may be augmented using a baseline shift by adding a constant noise value to the unipolar electrogram. The constant noise value may be sampled from a normal distribution.

A unipolar electrogram may be augmented using Gaussian noise by adding normal noise sampled from a Gaussian distribution the unipolar electrogram. The Gaussian distribution may have a standard deviation (e.g. 0.01) that is significantly smaller than the standard deviation (e.g. >0.5) of the unipolar electrogram signal.

A unipolar electrogram may be augmented by cropping by randomly replacing a segment of data in the unipolar electrogram with zeros. The start of the segment and its length are randomly sampled from a uniform distribution.

A unipolar electrogram may be augmented by resampling by resampling the unipolar electrogram into a lower frequency and adds zeros at the end of the signal. The padding is to maintain the resampled sequence of the same length.

As shown in FIG. 9, the unipolar electrogram data may be normalized prior to training. The normalization (e.g. min-max scaling) may also occur prior to augmenting the normalized unipolar electrogram data. The unipolar electrogram data may also be down-sampled prior to training and/or augmentation. For example, each unipolar electrogram may be down-sampled to 200 Hz using fast Fourier transformation. Then the magnitudes of each unipolar electrogram can be normalized through a min-max feature scaling.

In some examples, the deep learning neural network classification model may be trained using a combination of augmented and non-augmented unipolar electrograms.

In some examples, an augmentation probability may be defined to specify how often augmented data is input to train the deep learning neural network classification model. This may ensure that raw electrogram data is sufficiently observed by the neural network. For example, the augmentation probability may be set at 0.5 in some examples. This may specify the probability or frequency with which the inputs to the neural network are augmented vs. non-augmented.

In some cases, additional optimization techniques may be used to optimize the trained deep learning neural network classification model. For example, to optimize the trained model, the neural network may be initialized by He-initialization and optimized by Adam (see, for example, Kingma D P, Ba J. Adam: A method for stochastic optimization. arXiv:1412 6980 2014; December: [e-print]; and He K, Zhang X, Ren S, Sun J. Delving deep into rectifiers: Surpassing human-level performance on imagenet classification. Proceedings of the IEEE international conference on computer vision 2015; 1026-34).

At 340, the first location in the organ may be identified as a focal source location based on the unipolar electrogram classification result generated at 330. For example, the unipolar electrogram classification result can be compared to a focal source identification threshold parameter. When the unipolar electrogram classification result meets or exceeds the focal source identification threshold parameter, the first location in the organ can be identified as a focal source location.

In some examples, the deep learning neural network classification model may be defined to generate the unipolar electrogram classification result as a probability value that the unipolar electrogram corresponds to a focal source location. For instance, the unipolar electrogram classification result may be defined as a probability value on a continuous scale between 0 to 1 (or a sensitivity of 0% to 100%). The probability value may then be compared to a focal source identification threshold parameter that is defined as a specified probability value.

For example, the focal source identification threshold parameter may be defined to correspond to at least a sensitivity of 85%. In some examples, the focal source identification threshold parameter may be defined to correspond to a sensitivity in a range between about 85%-95%. In some examples, the focal source identification threshold parameter may be defined to correspond to a sensitivity of about 90%.

The focal source locations may then be displayed to a user, e.g. through a results interface on display 16. The results interface may illustrate the identified focal source locations in various ways, such as a classification result or a list or mapping of focal source locations. In some examples, the results interface may allow a user to review the identified focal source locations to assess whether any identified focal source locations may be false positives.

In some examples, the identified focal source locations may be used to guide ablation of those focal source locations. For instance, the operator unit 10 may be configured to guide ablation of the focal source locations using the ablation unit 44 through interfaces shown on display 16 and/or additional user feedback.

Testing Results

The example hierarchical method shown in FIG. 2A was previously applied in a randomized controlled trial that evaluated the efficacy of focal source location ablation as an adjunct to PVI in reducing AF recurrence compared to PVI alone in 80 patients with drug-refractory, high-burden paroxysmal or persistent AF (see for example Chauhan V S, Verma A, Nayyar S, Timmerman N, Tomlinson G, Porta-Sanchez A, Gizurarson S, Haider S, Suszko A, Ragot D, Ha A C T. Focal source and trigger mapping in atrial fibrillation: Randomized controlled trial evaluating a novel adjunctive ablation strategy. Heart Rhythm 2020 May; 17(5 Pt A):683-91). In this trial, antiarrhythmic drugs were held for 5 half-lives with the exception of amiodarone which was discontinued 1 month before mapping. LA mapping was performed during either spontaneous AF or induced AF using burst atrial pacing at CL 180-250 ms, and if necessary, intravenous isoprenaline (0.5-1 μg/min). Electroanatomic data was acquired using the CARTO™ (Biosense Webster, Diamond Bar, CA, United States) system and a roving 20-pole circular catheter (Lasso™ Nav Variable, 15-25 mm diameter, 1 mm electrodes at 2-6-2 mm spacing, Biosense Webster, Diamond Bar, CA, United States). Stable catheter-tissue contact and signal quality was ensured before recording 5-s bipolar (bandpass 30-500 Hz) and unipolar EGMs (bandpass 0.05-500 Hz) at a sampling rate of 1,000 Hz. Unipolar EGMs were recorded only from one electrode of the bipolar electrode pair. All EGMs were exported for off-line analysis of FaST sites using custom software written in Matlab™ (MathWorks Inc., Natick, MA, United States). Noisy EGMs with low signal:noise and EGMs recorded >5 mm from the LA endocardium were excluded to minimize far-field signal contamination.

Real-time endocardial mapping of the left atrium (LA) during sustained AF was completed in 78 patients. Electrical signal sets from these 78 patients were used to train and test an example implementation of the neural network classification model described herein above with respect to FIGS. 3 and 4. The results of this testing was then compared with numerous alternative methods for classifying electrograms as focal source locations or non-focal source locations.

The characteristics of the patients are summarized in Table 1 below. As shown in Table 1, the seventy-eight patients (age 61±10 years, 74% males) had either high-burden paroxysmal AF (51%) or persistent AF (49%). The LA volume and LV ejection fraction were 44±16 ml/m$^2$ and 59±8%, respectively. Mapping was performed during spontaneous AF in 36 (46%) patients and after inducing sustained AF with programmed atrial stimulation in the remaining 42 (54%) patients. On average, 340±60 LA sites from 60±8 circular catheter acquisitions were analysed per patient after excluding overlapping points and those with poor endocardial contact. Focal source locations were identified in all patients (4.9±1.9 per patient), including 2.1±1.1 PV focal source locations and 2.8±1.4 extra-PV focal source locations per patient.

TABLE 1

Baseline Patient Characteristics

| | All Patients (n = 78) | Training/ Validation Cohort (n = 58) | Testing Cohort (n = 20) | p-value |
|---|---|---|---|---|
| Age, years | 61 ± 10 | 61 ± 10 | 59 ± 8 | 0.229 |
| Male, n(%) | 58(74) | 42(72) | 16(80) | 0.503 |
| Body mass index, kg/m$^2$ | 29 ± 5 | 30 ± 5 | 29 ± 5 | 0.598 |
| LVEF, % | 59 ± 8 | 58 ± 9 | 61 ± 4 | 0.097 |
| LA dimensions | | | | |
| LA diameter, mm | 42 ± 7 | 42 ± 6 | 40 ± 8 | 0.383 |
| LA volume, ml | 90 ± 35 | 90 ± 33 | 91 ± 39 | 0.893 |
| LA volume index, ml/m$^2$ | 44 ± 16 | 43 ± 16 | 44 ± 16 | 0.811 |
| AF characteristics | | | | |
| High-burden paroxysmal, n(%) | 40(51) | 29(50) | 11(55) | 0.700 |
| Persistent, n(%) | 38(49) | 29(50) | 9(45) | 0.700 |
| Duration of AF, years | 5.6 ± 5.0 | 5.9 ± 5.0 | 4.6 ± 3.4 | 0.245 |
| Comorbidities | | | | |
| Diabetes, n(%) | 4(5) | 2(3) | 2(10) | 0.270 |
| Hypertension, n(%) | 37(47) | 25(43) | 12(60) | 0.192 |
| Sleep apnea, n(%) | 25(32) | 19(33) | 6(30) | 0.820 |
| Obesity, n(%) | 29(37) | 23(40) | 6(30) | 0.441 |
| Coronary artery disease, n(%) | 2(3) | 2(3) | 0(0) | 1.000 |
| Current antiarrhythmic drugs | | | | |
| Flecainide or propafenone, n(%) | 29(37) | 26(45) | 3(15) | 0.017 |
| Sotalol, n(%) | 6(8) | 5(9) | 1(5) | 1.000 |
| Amiodarone, n(%) | 21(27) | 14(24) | 7(35) | 0.345 |
| β-blocker, n(%) | 37(47) | 28(48) | 9(45) | 0.800 |
| Calcium channel blocker, n(%) | 15(19) | 9(16) | 6(30) | 0.192 |
| Number of failed AAD | 1.7 ± 0.9 | 1.7 ± 1.0 | 1.6 ± 0.8 | 0.482 |

Abbreviations: AAD-antiarrhythmic drugs; CL-cycle length; LA-left atrium; LVEF-left ventricular ejection fraction; obesity-BMI >30 kg/m$^2$; renal dysfunction-eGFR <50 ml/min/1.72 m$^2$ Focal source locations were identified in the electrograms acquired from the patients by manual classification of sustained periodic unipolar QS EGMs over 5 s. Among the 78 patients, a total of 13,184 periodic unipolar EGMs were recorded of which 1,220 (9.2%) had a dominant, sustained QS morphology (i.e. FaST) and the remaining 11,964 (90.7%) were non-FaST (FIG. 3).

FIG. 5 illustrates the division of the electrograms from the patients into training and testing cohorts. The patients (n=78) were randomly divided into a training/validation cohort (n=58) and test cohort (n=20). As shown in FIG. 5, all periodic unipolar EGMs were divided into the training (n=10,004) and testing cohorts (n=3,180). The deep learning neural network classification model was trained and validated using 10,004 periodic unipolar EGMs from a cohort of 58 patients, where the prevalence of focal source EGMs was 9.2%. Prior to training and testing, the periodic unipolar EGMs from both cohorts were initially down-sampled to 200 Hz using fast Fourier transformation. Then, their magnitudes were normalized through a min-max feature scaling.

Cross-validation in the training cohort was achieved using 5 different random seeds, such that each seed produced a different validation cohort and a different network initialization (i.e. 3-fold cross validation performed 5 times). The final deep learning neural network classification model was then tested using 3,180 periodic unipolar EGMs from a testing cohort of 20 patients, where the prevalence of focal source EGMs was 9.4%. The clinical characteristics of the validation and testing cohorts were similar as shown in Table 1.

Manual classification of focal source locations using the FaST algorithm (the example process shown in FIG. 2A) at the time of PVI served as the gold standard. Subsequently, two cardiologists independently performed blinded re-classification of periodic unipolar EGMs as focal source locations vs. non-focal source locations using the FaST algorithm in a subset of 100 EGMs, which included 50 random EGMs and 50 EGMs falsely classified by an implementation of the example classification model. The sensitivity and specificity of focal source location re-classification by the cardiologists was evaluated relative to the gold standard. Inter- and intraobserver agreement among the cardiologists in focal source location re-classification was assessed using the kappa statistic.

In the results discussed below, continuous variables are presented as mean±standard deviation. Comparison between patient cohorts was done using an unpaired t-test or Mann-Whitney U test where appropriate. Receiver operator characteristic (ROC) analysis was performed to evaluate the diagnostic performance of the deep learning neural network classification model for detecting focal source locations with results presented as area under the curve (AUC) and 95$^{th}$ percentile confidence interval (95% CI). Specificity was calculated at prespecified sensitivities of 85, 90 and 95% as well as the sensitivity (78%) of cardiologists re-classifying a subset of 50 random periodic unipolar electrograms. In order to complement ROC analysis for class-imbalanced datasets, the performance of the deep learning neural network classification model was evaluated using the F1-score which is a harmonic mean of the positive predictive value and sensitivity (see for example Saito T, Rehmsmeier M. The precision-recall plot is more informative than the ROC plot when evaluating binary classifiers on imbalanced datasets. PLoS One 2015; 10(3):e0118432). A 2-tailed p-value <0.05 was considered statistically significant. Statistical analyses were performed using scikit-learn (see for example Pedregosa F, Varoquaux G, Gramfort A, Michel V, Thirion B, Grisel O, Blonde) M, Prettenhofer P, Weiss R, Dubourg V, Vanderplas J. Scikit-learn: Machine learning in Python. Journal of Machine Learning Research 2011; 12:2825-30).

FIGS. 6A-6D illustrates plots of the performance of the classification model in identifying focal source locations. The plots shown in FIGS. 6A-6D include receiver operating characteristic curves, or ROC curves, that illustrate the diagnostic ability of a binary classifier system as a discrimination threshold is varied. The area under the curve (AUC) in the ROC curves illustrates represents the degree or measure of separability of the system.

Figure 6A:
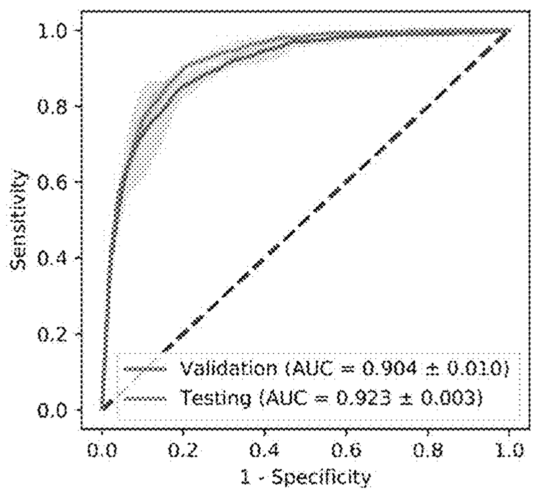
FIG. 6A illustrates an ROC plot of focal source identification results generated using an example implementation of the focal source identification methods described herein.

The performance of the example deep learning neural network classification model in classifying focal source locations and non-focal source locations for the 3-fold cross-validation and testing cohorts is demonstrated by the ROC curve in FIG. 6A. The example deep learning neural network classification model achieved a high ROC AUC of 0.904+1-0.010 (95% CI 0.884, 0.924) and 0.923 (95% CI 0.917, 0.929) in validation (3-fold cross-validation and testing cohorts, respectively. The AUC variance for the test cohort was <0.5% demonstrating robustness of the example deep learning neural network classification model.

In addition, the performance of classic machine learning models used to classify focal source locations, including logistic regression, support vector machine (SVM) and k nearest neighbor (KNN) was evaluated. Compared to the example deep learning neural network classification model described herein, these classic models have a lower model complexity, which limits their ability to analyze complex data, such as EGMs. The SVM and KNN models were evaluated with 2 different hyper-parameters, where the polynomial degree is either 3 or 10 for SVM, and the number of k neighbors is either 10 or 50 for KNN. These classic models were implemented through scikit-learn.

Figure 6B:
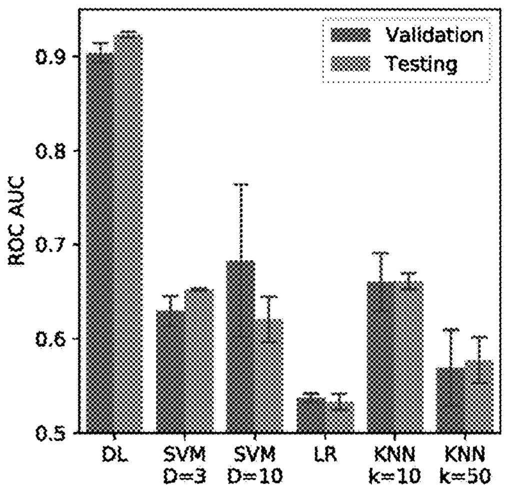
FIG. 6B illustrates a plot of focal source identification results generated using an example implementation of the focal source identification methods described herein as well as examples of focal source identification methods using alternative machine learning models.

As shown in FIG. 6B and Table 2, the performance of classic machine learning models, including logistic regression (LR), SVM and KNN, was inferior to that of the example deep learning neural network classification model based on a lower ROC AUC, specificity and F1-score. FIG. 6B illustrates a plot of the ROC AUC for the example deep learning neural network classification model and classic machine learning models. The error bars indicate standard deviation of different random seeds.

TABLE 2

Performance of Various Supervised ML models in Detecting FaST

| Methods | AUC | Predefined Sensitivity* | Specificity | F1-score |
|---|---|---|---|---|
| Example model | 0.923 (0.917-0.929) | 78* | 88.8 (87.4-90.3) | 0.549 (0.522-0.576) |
| SVM D = 3 | 0.652 (0.649-0.655) | 78 | 33.5 (33.2-33.8) | 0.187 (0.156-0.218) |
| SVM D = 10 | 0.620 (0.572-0.669) | 78 | 30.5 (27.4-33.6) | 0.169 (0.135-0.204) |
| Logistic regression | 0.533 (0.517-0.550) | 78 | 26.3 (25.1-27.5) | 0.121 (0.091-0.151) |
| KNN k = 10 | 0.661 (0.644-0.677) | 78 | 35.1 (33.3-36.9) | 0.211 (0.191-0.231) |
| KNN k = 50 | 0.577 (0.529-0.626) | 78 | 28.3 (25.5-30.1) | 0.135 (0.103-0.167) |

*Benchmark sensitivity achieved by cardiologist re-classifying FaST in 50 randomly selected EGMs; AUC-area under curve; KNN-k nearest neighbors; ML-machine learning; SVM-support vector machine As illustrated, the performance of classic machine learning models, such as logistic regression, SVM and KNN, in classifying focal source locations was inferior to that of the described classification model, which highlights the computational proficiency of described classification model in electrogram classification without the requisite for discrete feature input, such as unipolar EGM onset.

The performance of the example deep learning neural network classification model in classifying focal source locations was also evaluated using different prediction thresholds. Because the example deep learning neural network classification model can be configured to generate a continuous output, ranging from 0 to 1, the model output was classified as a focal source location when the DL output was above a threshold, which was based on achieving a predefined sensitivity of 85%, 90% or 95% in detecting focal source locations. The respective specificity, positive predictive value (PPV), negative predictive value (NPV), F1-score and accuracy are shown in Table 3.

TABLE 3

Performance of DL Model

| | FaST Prevalence | Defined Sensitivity | Specificity | PPV | NPV | F1-score | Accuracy |
|---|---|---|---|---|---|---|---|
| Cross-Validation Cohort | 9.2% (n = 1, 220) | 78* | 87.3 (81.0-93.5) | 40.0 (30.9-49.1) | 97.4 (97.0-97.9) | 0.528 (0.448-0.607) | 86.4 (80.7-92.1) |
| | | 85 | 81.2 (75.9-86.6) | 32.1 (28.7-35.6) | 97.9 (97.6-98.3) | 0.464 (0.429-0.499) | 81.5 (76.8-86.2) |
| | | 90 | 73.7 (69.7-77.7) | 26.3 (22.9-29.8) | 98.5 (98.3-98.6) | 0.406 (0.365-0.447) | 75.2 (71.7-78.7) |
| | | 95 | 60.3 (54.9-65.7) | 20.0 (18.8-21.2) | 99.0 (98.7-99.3) | 0.330 (0.313-0.347) | 63.6 (58.9-68.2) |
| Testing Cohort | 9.4% (n = 300) | 78* | 88.8 (87.4-90.3) | 42.3 (39.1-45.5) | 97.5 (97.5-97.6) | 0.549 (0.522-0.576) | 87.9 (86.5-89.2) |
| | | 85 | 85.0 (83.2-86.9) | 36.7 (34.2-39.2) | 98.0 (97.7-98.3) | 0.509 (0.486-0.532) | 84.9 (83.3-86.4) |
| | | 90 | 81.9 (81.8-82.0) | 33.6 (33.3-33.9) | 98.5 (98.4-98.6) | 0.486 (0.481-0.491) | 82.5 (82.3-82.6) |
| | | 95 | 68.7 (61.4-76.1) | 24.1 (19.8-28.4) | 99.1 (99.1-99.2) | 0.383 (0.330-0.437) | 71.1 (64.6-77.7) |

Abbreviations:

*sensitivity of cardiologist re-classifying FaST from a subset of 50 random periodic unipolar EGMs;

NPV-negative predictive value;

PPV-positive predictive value;

95% confidence intervals presented in parentheses

The example deep learning neural network classification model had reasonably high specificity for each predefined sensitivity. In the case of 90% sensitivity, the example deep learning neural network classification model achieved a specificity of 81.9% (95% CI 81.8-82.0%), PPV of 33.6% (95% CI 33.3-33.9%), NPV of 98.5% (CI 95% 98.4-98.6%), F1-score of 0.486 (CI 95% 0.481-0.491), and an accuracy of 82.5% (95% CI 82.3, 82.6). Because the deep learning model performance tends to improve with larger training datasets (see for example LeCun Y, Bengio Y, Hinton G. Deep learning. Nature 2015; 521(7553):436-44), the performance of the example deep learning neural network classification model was further evaluated using smaller training cohorts.

Figure 6C:
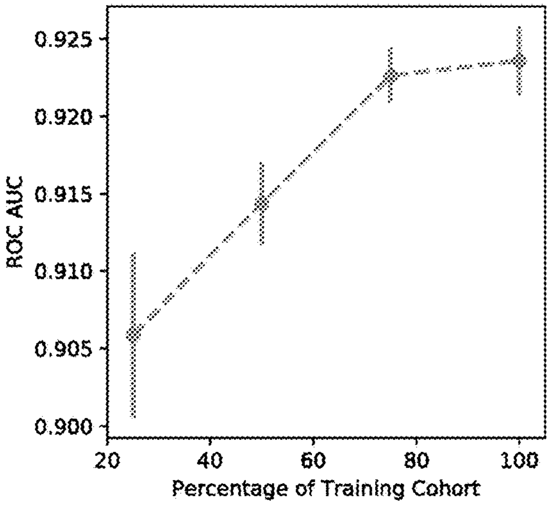
FIG. 6C illustrates an ROC plot of focal source identification results generated using an example implementation of the focal source identification methods as a function of the training cohort size.

FIG. 6C illustrates a plot of the ROC AUC for the example deep learning neural network classification model as a function of the training cohort size. As shown in FIG. 6C, the ROC AUC significantly improved when the test cohort size was increased from 25 to 75% of the original sample size. However, a further increase from 75 to 100% was associated with a marginal change in ROC AUC from 0.921 to 0.923, respectively, suggesting that the training cohort of 58 patients that was used to generate test results was adequately sized.

The reliability in focal source location re-classification was evaluated in a random sample of 50 periodic unipolar EGMs from 18 patients by 2 cardiologists. In this 50 EGM subset, the proportion with focal source location was modest at 18%. Intra- and interobserver variability was moderate based on a kappa of 0.43 and 0.46, respectively, but intraobserver variability improved (kappa 0.81) after the cardiologists reviewing their disagreements and retrained. Among these 50 EGMs, the example deep learning neural network classification model's classification of focal source locations had an ROC AUC of 0.927 ($95^{th}$ CI 0.916, 0.938), which was similar to that of the whole periodic unipolar EGM dataset.

Figure 6D:
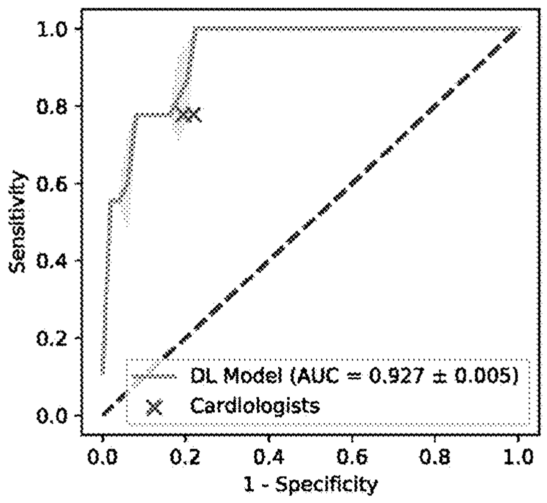
FIG. 6D illustrates a plot of focal source identification results generated using an example implementation of the focal source identification methods described herein as well as an example of a focal source identification method that includes manual classification by cardiologists.

FIG. 6D illustrates a plot of the ROC curve for focal source classification using the example deep learning neural network classification model in the random sample of 50 periodic unipolar EGMs. The performance of 2 cardiologists for focal source re-classification is also plotted for comparison. In the subset of 50 random EGMs, the sensitivity and specificity in classifying focal source locations with the example deep learning neural network classification model was 78.1 ($95^{th}$ CI 77.6, 78.7) and 82.2 ($95^{th}$ CI 80.0, 84.4), respectively, which was similar to that of the cardiologists (sensitivity 77.8, specificity 79.0) (see FIG. 6D). Among the EGMs with interobserver agreement (n=35 of 50), the example deep learning neural network classification model's classification of focal source locations had a higher ROC AUC of 0.980 ($95^{th}$ CI 0.980, 0.986).

As noted above, the example neural network structure was defined with 18 layers of nodes. The inventors determined that a neural network structure with 18 layers provided superior results when compared to neural networks using additional layers (e.g. a 50-layer network such as a network structure based on ResNet-50, and a 101 layer network such as a network structure based on ResNet-101). In addition, the example residual convolutional neural network structure illustrated in FIG. 4 was found to provide superior results when compared to alternative neural network architectures such as an EfficientNet architecture. A comparison of the testing performance in classifying focal source locations is shown in Table 4.

TABLE 4

Performance of Various Convolutional Neural Network Architectures in Detecting Focal Source Locations

| Methods | AUC | Predefined Sensitivity* | Specificity | F1-score |
|---|---|---|---|---|
| Example neural network structure | 0.923 (0.917-0.929) | 78* | 88.8 (87.4-90.3) | 0.549 (0.522-0.576) |
| ResNet-50 | 0.915 (0.905-0.925) | 78 | 88.0 (86.6-89.4) | 0.529 (0.500-0.558) |
| ResNet-101 | 0.907 (0.892-0.923) | 78 | 87.5 (85.5-89.5) | 0.501 (0.475-0.528) |
| EfficientNet-B0 | 0.919 (0.913-0.925) | 78 | 88.3 (86.9-89.7) | 0.535 (0.512-0.558) |
| EfficientNet-B1 | 0.913 (0.901-0.925) | 78 | 87.9 (86.3-89.5) | 0.520 (0.501-0.539) |

*Benchmark sensitivity achieved by cardiologist re-classifying focal source locations in 50 randomly selected EGMs; AUC-area under curve; CNN-convolutional neural network The deep learning neural network classification model was also evaluated to determine the effectiveness of training the model using data augmentations. In a first test, artificial data augmentations were implemented, namely baseline shifting, Gaussian noise, cropping and resampling to the unipolar electrograms while artificial data augmentations were omitted in a separate test. A hyper-parameter was introduced to track the probability of augmentation and to ensure that both clean and noised examples were observed during training. The trained deep learning neural network classification model was finally evaluated in the testing cohort.

Figure 10:
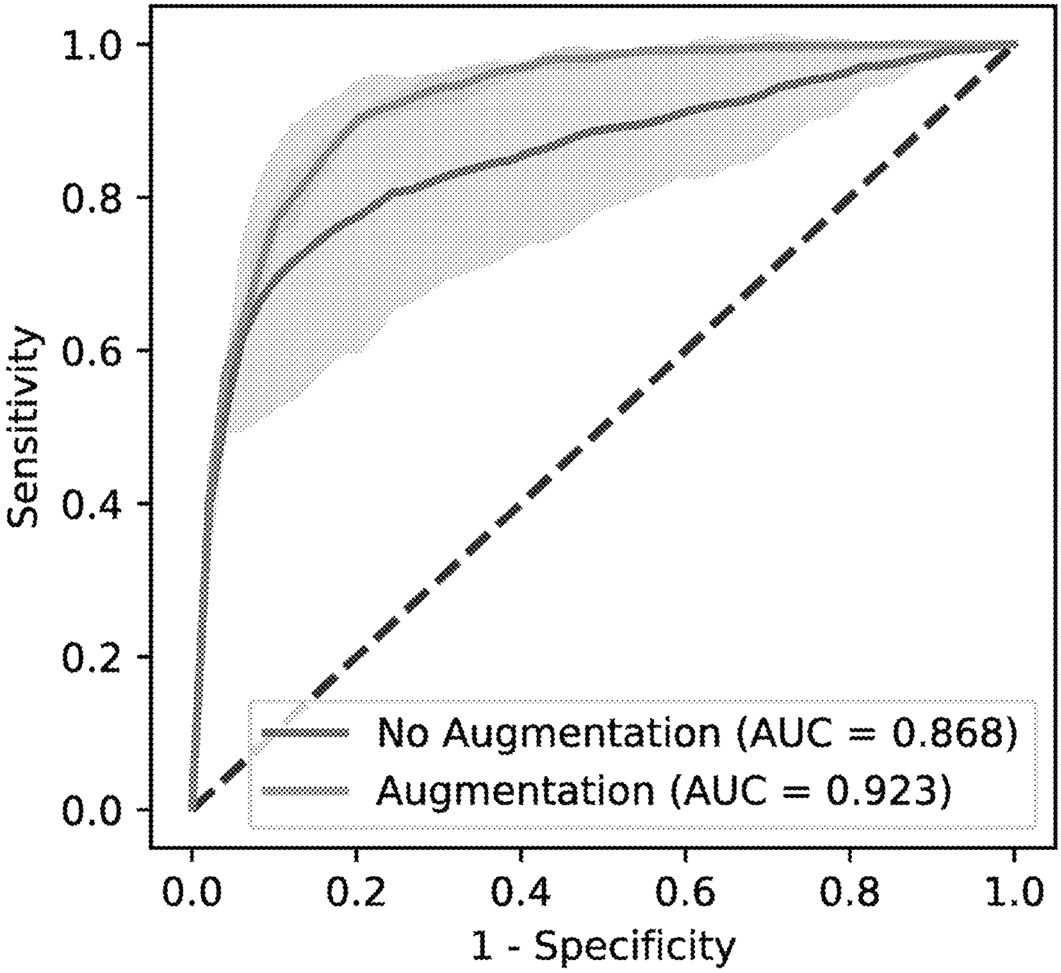
FIG. 10 illustrates an ROC plot of focal source identification results generated using an example implementation of the focal source identification methods described herein when an example neural network model is trained with an augmented signal set and when the example neural network model is trained without an augmented signal set.

To evaluate the effectiveness of augmentation, the performance of the deep learning neural network classification model was compared when trained was performed with and without augmented data. The same training scheme was implemented with and without augmented data. As shown in FIG. 10, the implementation of the classification model trained without augmentation had an ROC AUC of 0.868, which was less than that of the implementation of the classification model trained with data augmentations (0.923).

In many circumstances, deep learning models are considered to operate as a black box without much in the way of explainability. This can discourage adoption of deep learning models. However, the inventors have identified that the deep learning neural network classification model described herein can be analyzed such that the classification results can be readily evaluated and explained to a user. In particular, a gradient-based method (Grad-CAM) may be used to explain the classification results on unipolar electrograms. This may promote uptake since the classification results can be demystified for users of the classification model.

For example, a gradient-weighted class activation mapping method (Guided Grad-CAM, see for example Selvaraju R R, Cogswell M, Das A, Vedantam R, Parikh D, Batra D. Grad-CAM: Visual Explanations from Deep Networks via Gradient-based Localization. Proceedings of the IEEE international conference on computer vision 2017; 618-26) may be used to probe important features and explain the model's classification results as focal source vs. non-focal source. Grad-CAM is commonly used in computer vision to provide a contextual explanation for model decisions. Grad-CAM defines the importance of a feature based on the changes in the classification output in response to a small variance or gradient in the feature. A larger change in output indicates that this feature is more important. Grad-CAM may be similarly applied to the classification models described herein due to similarities in architecture with models used for computer vision applications.

A gradient-based method was applied to interpret the deep learning neural network classification model described herein. The gradient-based interpretation demonstrated accurate tracking of unipolar QS complexes by select convolutional layers of the model. In particular, the inventors used Grad-CAM to probe the gradient in the convolutional layer of the residual blocks of the deep learning neural network classification model described herein. Grad-CAM may be advantageous in evaluating the model explainability because the whole EGM signal is considered and the contribution of convolutional layers are weighted to generate visually interpretable importance plot.

Figure 8A:
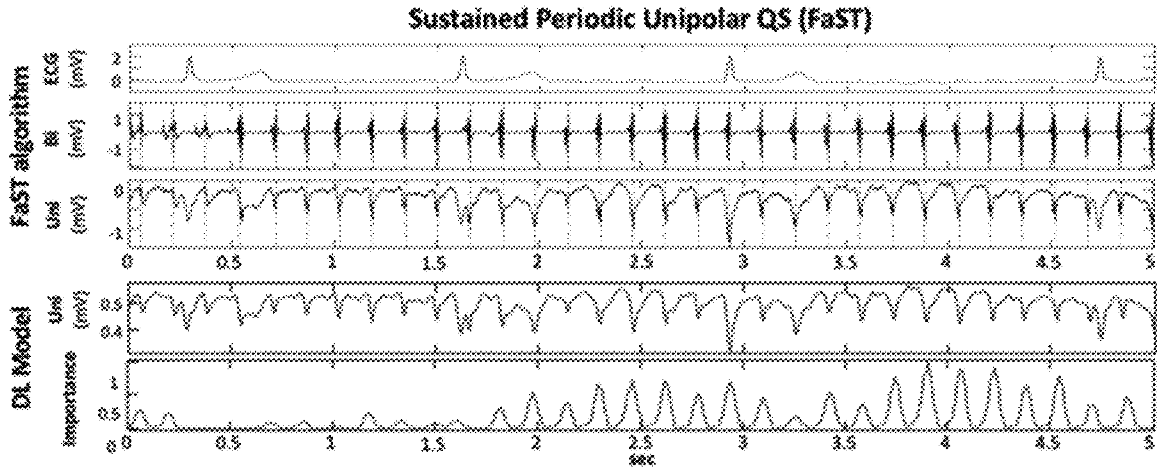
FIG. 8A illustrates example plots of a unipolar electrogram, a bipolar electrogram and an ECG lead V1 received from a recording site in a patient with a sustained periodic unipolar QS morphology and the corresponding output of an implementation of the example focal source identification methods described herein.
Figure 8B:
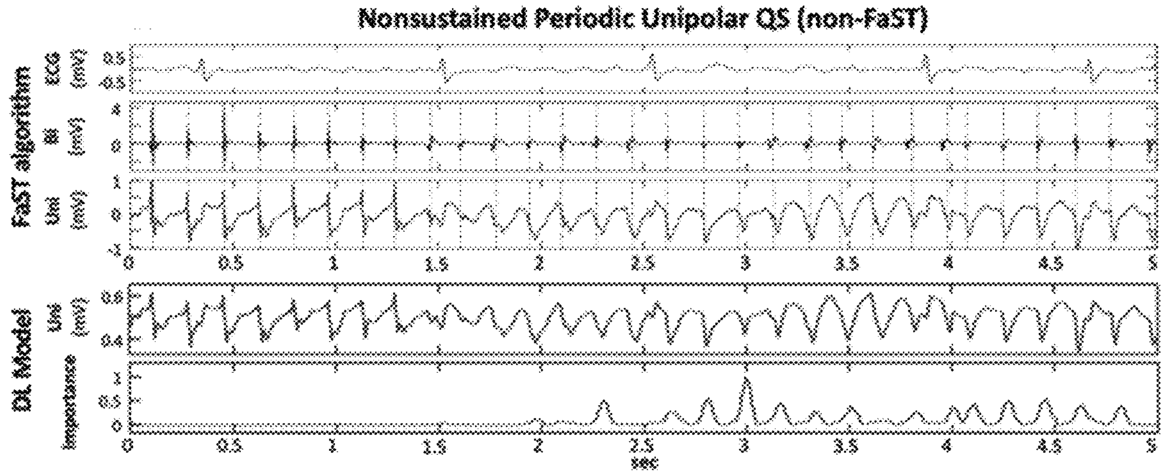
FIG. 8B illustrates example plots of a unipolar electrogram, a bipolar electrogram and an ECG lead V1 received from a recording site in a patient with a non-sustained periodic unipolar QS morphology and the corresponding output of an implementation of the example focal source identification methods described herein.
Figure 8C:
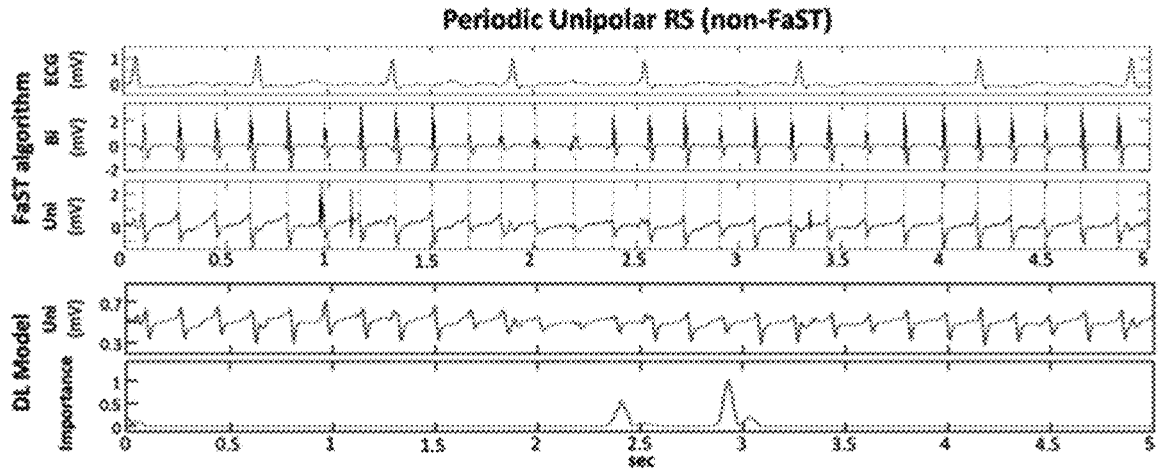
FIG. 8C illustrates example plots of a unipolar electrogram, a bipolar electrogram and an ECG lead V1 received from a recording site in a patient with a periodic unipolar RS morphology and the corresponding output of an implementation of the example focal source identification methods described herein.

From the subset of 100 periodic unipolar EGMs used above to evaluate observer reliability and false classification of focal source locations, a random sample of 10 EGMs were input into Grad-CAM in order to determine which convolutional layers of the classification model described herein best tracked unipolar QS complexes. The results of this analysis indicate that Grad-CAM's importance plot from convolutional layer 3 identified atrial unipolar QS complexes most consistently in all 10 EGMs. FIGS. 8A-8C show 3 examples of periodic unipolar EGMs from focal source and non-focal source location where EGM onset is annotated with a vertical red line using the FaST algorithm illustrated in FIG. 2A. As shown in FIGS. 8A-8C, the importance of features was visualized as a 1-D importance plot where peaks indicated more importance. In each example, the importance plot from convolutional layer 3 demonstrates periodic peaks of importance that coincide temporally to most atrial unipolar QS complexes, while ignoring atrial unipolar RS complexes and far-field ventricular unipolar QS complexes. These importance plots provide a visual explanation of the example classification model's classification of focal sources vs. non-focal source.

FIG. 8A illustrates plots from a focal source location identified using the FaST algorithm based on sustained, periodic unipolar QS for 5-seconds. The Bipolar EGM and unipolar EGM are shown with dashed, red vertical lines annotating periodic activations. The described classification model receives as an input the raw unipolar EGM without annotations. The importance plot from convolutional layer 3.0 demonstrates peaks corresponding to the majority of atrial unipolar QS complexes, but not the far-field ventricular complexes during the 5-second recording.

FIG. 8B illustrates plots from a non-focal source location identified using the FaST algorithm based on non-sustained periodic unipolar QS. As shown, the first 8 complexes are unipolar RS, while the rest are unipolar QS. The importance plot from the convolutional layer 3.0 demonstrates peaks corresponding to the majority of atrial unipolar QS complexes, but not the atrial unipolar RS complexes.

FIG. 8C illustrates plots from a non-focal source location identified using the FaST algorithm based on the absence of unipolar QS complexes. Accordingly, the importance plot from the convolutional layer 3.0 demonstrates virtually no peaks. There are 2 peaks which correspond to atrial unipolar rS complexes, similar in morphology to QS complexes.

The evaluation of the classification model using Grad-CAM indicated that the higher convolutional layers are more relevant in periodic unipolar QS classification, and in distinguishing atrial EGMs from far-field ventricular EGMs. These layers also detect the presence of sustained periodicity, which adds temporal dimensionality to the detection of individual unipolar QS complexes.

The deep learning neural network classification model described herein automatically classified periodic unipolar EGMs with sustained QS complexes (i.e. focal source location) during AF without the requisite for EGM segmentation or annotation. The described model's accuracy in focal source classification was 82.5% (ROC AUC of 92.3), which is high considering the low prevalence of focal source EGMs (9%) and the spatiotemporal variability in unipolar EGM morphologies. False detection of focal source locations may be attributed to ambiguous, time-varying unipolar EGM signal features, however in these instances the reliability in re-classifying focal source locations was also poor among cardiologists, indicating that the performance of the classification model was on par with that of the cardiologists. For select EGMs, introspection of the model convolutions identified the layer that tracked individual periodic unipolar QS EGMs, thereby providing visual verification of the model performance.

In previous approaches, unipolar QS classification is typically still performed manually and therefore susceptible to interpretation by the cardiologist, especially when morphology features are ambiguous, albeit periodic. This accounts for the moderate intra- and interobserver agreement in focal source re-classification in a random subset of periodic unipolar EGMs (kappa 0.43-0.47), and essentially no intra- or interobserver agreement in a subset falsely classified by the classification model described herein. However, intraobserver agreement did improve (kappa 0.71-0.81) after cardiologists were retrained. These findings highlight the modest precision in the manual interpretation and classification of periodic unipolar QS EGMs during AF.

Despite this inherent limitation, the classification model described herein achieved good performance in classifying focal sources based on an ROC AUC >90% in the training and testing cohorts. This performance was similar when assessed in 75% of the training cohort indicating that data satisfaction was reached and that a larger training cohort would be unlikely to significantly improve classification accuracy. Based on the ROC AUC, this performance was also comparable to re-classification by cardiologists. False negative classification of FaST by the classification model was commonly due to fractionation at unipolar EGM onset and low amplitude/slew unipolar EGMs near the PV ostia. In false positive cases, periodic unipolar EGMs manifested small rS complexes or were nonsustained for only a few beats and bordered on the prespecified criteria of >90% temporal stability for 5-seconds.

Figure 7A:
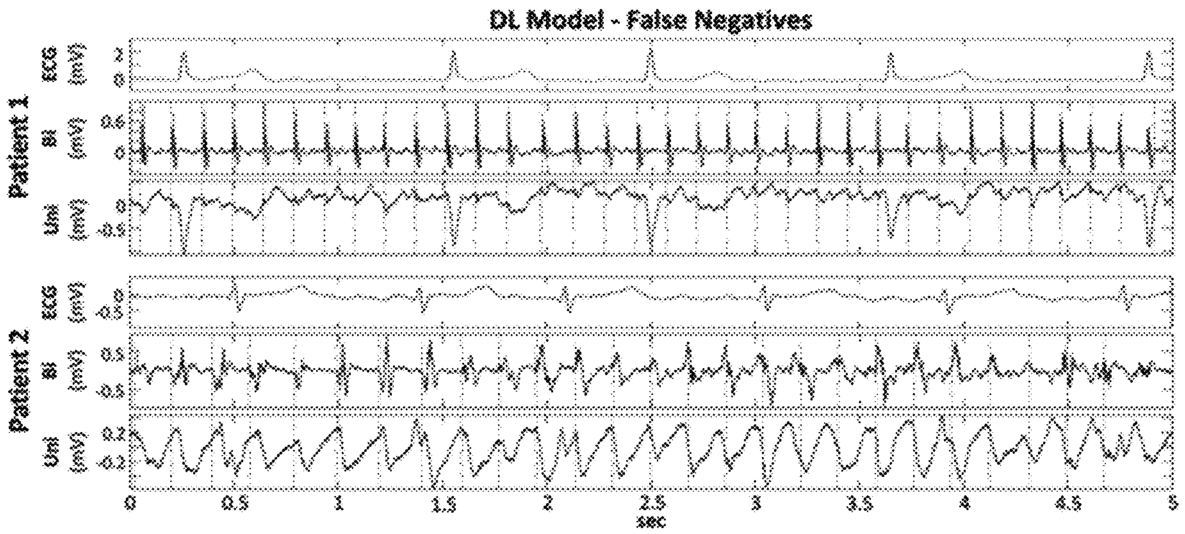
FIG. 7A illustrates example plots of a unipolar electrogram, a bipolar electrogram and an ECG lead V1 received from recording sites in patients where the example focal source identification methods described herein generated false negative results.
Figure 7B:
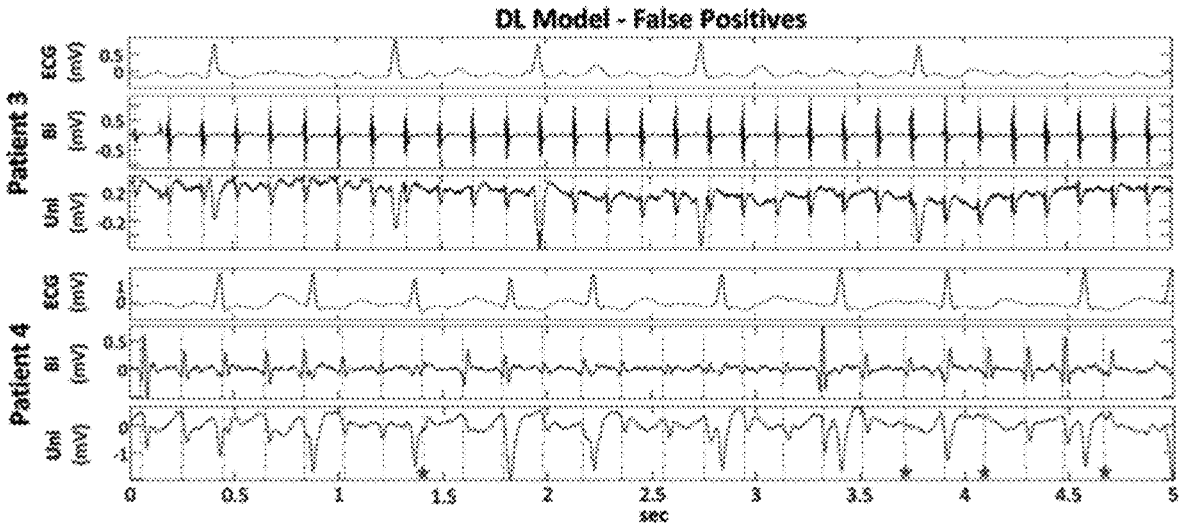
FIG. 7B illustrates example plots of a unipolar electrogram, a bipolar electrogram and an ECG lead V1 received from recording sites in patients where an implementation of the example focal source identification methods described herein generated false negative results.

FIGS. 7A-7B illustrate example plots of signal sets from patients that were incorrectly classified as non-focal source locations (FIG. 7A) or focal source locations (FIG. 7B). FIG. 7A illustrates false negative classification of focal sources using the described classification model may be due to low-amplitude, sustained periodic unipolar QS complexes near PV ostium (Patient 1, top panel) and broad, slurred unipolar QS complexes (Patient 2, bottom panel). FIG. 7B illustrates false positive classification of focal sources using the described classification model due to sustained unipolar rS complexes with small r waves (Patient 3, top panel) and near-sustained periodic unipolar QS complexes (red stars—rS complexes) (Patient 4, bottom panel).

In order to evaluate the basis for the false classification of focal source locations and non-focal source locations by the described classification model, a subset of 50 periodic unipolar EGMs were selected, which comprised 25 false negative EGMs with the lowest model predicted probability for focal source, and 25 false positive EGMs with the highest model predicted probability for focal source. False positive classification by the described classification model was commonly due to borderline EGMs with small rS complexes or nonsustained periodicity. In contrast, false negative cases by the described classification model were most often the result of EGM fractionation or low amplitude/slewed QS complexes, such as near the PV ostium as shown in FIG. 7A. Given the complexity of these EGMs, the reliability in focal source location re-classification was assessed by 2 cardiologists. In this 50 EGM subset, the proportion with focal sources was 50%, which included all 25 false negative EGMs. Intra- and interobserver variability in focal source re-classification was poor based on a kappa of −0.08 and −0.02, respectively, which was concordant with the false classification or disagreement with the described classification model. However, intraobserver agreement among the 2 cardiologists improved (kappa 0.71) after they reviewed disagreements and retrained.

Focal sources may be a relevant mechanism sustaining AF in some patients, which provides the rationale for accurate focal source identification. Given the complexity and non-stationarity of AF EGMs, automating focal source detection is difficult using multisite EGM recordings and conventional time-frequency domain analysis. Manual overreading may improve the robustness of focal source detection, but this is time-consuming and still susceptible to imprecision.

As described herein, automated focal source detection using a deep learning neural network model using a training set of periodic unipolar EGMs was shown to be accurate. A fully automated approach such as that described herein can improve interobserver variability and reduce the time required to identify focal source locations. As a clinical detection tool, high sensitivity is important to identify the majority of putative focal sources, but equally important is the need to visually verify the EGM output so false positives are discarded. At a prespecified sensitivity of 90%, the specificity and accuracy of focal source detection with the described classification model was high at 82% and 83%, respectively. Thus, the described classification model may improve clinical AF detection and/or mapping workflows by efficiently generating a comprehensive list of focal source locations.

While the above description provides examples of the embodiments, it will be appreciated that some features and/or functions of the described embodiments are susceptible to modification without departing from the spirit and principles of operation of the described embodiments. Accordingly, what has been described above has been intended to be illustrative of the invention and non-limiting and it will be understood by persons skilled in the art that other variants and modifications may be made without departing from the scope of the invention as defined in the claims appended hereto. The scope of the claims should not be limited by the preferred embodiments and examples, but should be given the broadest interpretation consistent with the description as a whole.

The invention claimed is:

1. A method of identifying one or more focal source locations of electrophysiological activity for an organ, the method comprising:

receiving, by a processor, a first electrical signal set obtained from a first location of the organ within a living patient, wherein the first electrical signal set comprises an entire unipolar electrogram;

determining, by the processor, that the first electrical signal set is periodic;

upon determining that the first electrical signal set is periodic, generating, by the processor, a unipolar electrogram classification result by inputting the entire unipolar electrogram to a deep learning artificial neural network classification model wherein the deep learning artificial neural network classification model is trained to generate the unipolar electrogram classification result in response to receiving the entire unipolar electrogram as an input;

identifying, by the processor, the first location in the organ as a first focal source location of the one or more focal source locations based on the unipolar electrogram classification result; and outputting focal source location data including the identified first focal source location, wherein the focal source location data is usable to guide ablation of the one or more focal source locations;

wherein the deep learning artificial neural network classification model is trained using unipolar electrogram data acquired in vivo from a cohort of training patients.

2. The method of claim 1, wherein identifying the first location in the organ as the first focal source location comprises:

(a) comparing the unipolar electrogram classification result to a focal source identification threshold parameter; and (b) identifying the first location in the organ as the first focal source location of the one or more focal source locations when the unipolar electrogram classification result meets or exceeds the focal source identification threshold parameter.

3. The method of claim 2, wherein (a) the deep learning artificial neural network classification model is configured to generate the unipolar electrogram classification result as a probability value that the entire unipolar electrogram corresponds to a focal source location of the one or more focal source locations; and (b) the focal source identification threshold parameter corresponds to a sensitivity of at least 85%.

4. The method of claim 3, wherein the focal source identification threshold parameter corresponds to a sensitivity in a range between about 85%-95%.

5. The method of claim 4, wherein the focal source identification threshold parameter corresponds to a sensitivity of about 90%.

6. The method of claim 1, wherein the deep learning artificial neural network classification model is configured to generate the unipolar electrogram classification result using only the unipolar electrogram as an input from the first electrical signal set.

7. The method of claim 1, wherein the deep learning artificial neural network classification model uses a residual convolutional artificial neural network.

8. The method of claim 7, wherein the residual convolutional artificial neural network is defined using one-dimensional convolution filters.

9. The method of claim 1, wherein the deep learning artificial neural network classification model uses an artificial neural network having 18 layers of neural nodes.

10. The method of claim 1, wherein the deep learning artificial neural network classification model is trained using raw unipolar electrogram data.

11. The method of claim 1, wherein the deep learning artificial neural network classification model is trained using augmented unipolar electrogram data.

12. The method of claim 1, further comprising:

receiving a plurality of additional electrical signal sets, each of the additional electrical signal sets being obtained from different locations in the organ, and each of the additional electrical signal sets comprising an additional unipolar electrogram;

determining that a given additional electrical signal set is periodic;

upon determining that the given additional electrical signal set is periodic, generating an additional unipolar electrogram classification result by inputting the additional unipolar electrogram from that given additional electrical signal set to the deep learning artificial neural network classification model; and identifying an additional location in the organ that corresponds to the given additional electrical signal set as an additional focal source location of the one or more focal source locations based on the additional unipolar electrogram classification result.

13. The method of claim 1, wherein the organ is a heart.

14. A system for identifying one or more focal source locations of electrophysiological activity for an organ, the system comprising:

an input operable to receive a first electrical signal set obtained from a first location of the organ within a living patient, wherein the first electrical signal set comprises an entire unipolar electrogram;

a processor coupled to the input, the processor configured to receive the first electrical signal set from the input and to determine that the first electrical signal set is periodic; upon determining that the first electrical signal set is periodic, generate a unipolar electrogram classification result by inputting the entire unipolar electrogram to a deep learning artificial neural network classification model wherein the deep learning artificial neural network classification model is trained to generate the unipolar electrogram classification result in response to receiving the entire unipolar electrogram as an input; and identify the first location in the organ as a first focal source location of the one or more focal source locations based on the unipolar electrogram classification result; and an output coupled to the processing unit, wherein the output is configured to output focal source location data including any identified focal source locations for the organ wherein the focal source location data is usable to guide ablation of the one or more focal source locations;

wherein the deep learning artificial neural network classification model is trained using unipolar electrogram data acquired in vivo from a cohort of training patients.

15. The system of claim 14 further comprising an ablation unit usable to perform catheter ablation, wherein the system is configured to guide catheter ablation of the one or more focal source locations.

16. A data processing system comprising:

(a) a non-transitory computer readable medium storing computer readable instructions and a data structure defining a deep learning artificial neural network classification model configured to generate a unipolar electrogram classification result, wherein the data structure comprises a plurality of nodes, each node having a node input and a node output, and the plurality of nodes being arranged into a plurality of layers of nodes including at least one input layer and at least one output layer; and (b) a computer processor operable to execute the computer readable instructions stored on the computer readable medium using the data structure to identify one or more focal source locations of electrophysiological activity for an organ;

wherein the computer readable instructions are defined to configure the computer processor to:

receive a first electrical signal set obtained from a first location of the organ within a living patient, wherein the first electrical signal set comprises an entire unipolar electrogram;

determine that the first electrical signal set is periodic;

upon determining that the first electrical signal set is periodic, input the entire unipolar electrogram to the data structure;

receive the unipolar electrogram classification result as an output from the data structure;

identify the first location in the organ as a first focal source location of the one or more focal source locations based on the unipolar electrogram classification result; and outputting focal source location data including the identified first focal source location, wherein the focal source location data is usable to guide ablation of the one or more focal source locations;

wherein the deep learning artificial neural network classification model is trained using unipolar electrogram data acquired in vivo from a cohort of training patients.

17. The data processing system of claim 16, wherein the deep learning artificial neural network classification model is defined by training the data structure using raw unipolar electrogram data.

18. The data processing system of claim 16, wherein the computer readable instructions are defined to configure the computer processor to identify the first location in the organ as the first focal source location by:

(a) comparing the unipolar electrogram classification result to a focal source identification threshold parameter; and (b) identifying the first location in the organ as the first focal source location of the one or more focal source locations when the unipolar electrogram classification result meets or exceeds the focal source identification threshold parameter.

19. The data processing system of claim 16, wherein the deep learning artificial neural network classification model is defined to generate the unipolar electrogram classification result using only the unipolar electrogram as an input from the first electrical signal set.

20. The data processing system of claim 16, wherein the computer readable instructions are defined to configure the computer processor to:

receive a plurality of additional electrical signal sets, each of the additional electrical signal sets being obtained from different locations in the organ, and each of the additional electrical signal sets comprising an additional unipolar electrogram;

determine that a given additional electrical signal set is periodic;

upon determining that the given additional electrical signal set is periodic, input the additional unipolar electrogram from that given additional electrical signal set to the data structure;

receive an additional unipolar electrogram classification result as an additional output from the data structure; and identify an additional location in the organ that corresponds to the given additional electrical signal set as an additional focal source location of the one or more focal source locations based on the additional unipolar electrogram classification result.

* * * * *